(12) United States Patent
Liang et al.

(10) Patent No.: US 11,013,736 B2
(45) Date of Patent: *May 25, 2021

(54) ORAL SOLID PREPARATION AND USE THEREOF

(71) Applicant: WUHAN LL SCIENCE AND TECHNOLOGY DEVELOPMENT CO., LTD., Hubei (CN)

(72) Inventors: Lei Liang, Hubei (CN); Yongkai Chen, Hubei (CN); Liu Hu, Hubei (CN); Wei Feng, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/317,508

(22) PCT Filed: Jul. 28, 2017

(86) PCT No.: PCT/CN2017/094988
§ 371 (c)(1),
(2) Date: Jan. 11, 2019

(87) PCT Pub. No.: WO2018/019300
PCT Pub. Date: Feb. 1, 2018

(65) Prior Publication Data
US 2019/0314368 A1 Oct. 17, 2019

(30) Foreign Application Priority Data

Jul. 29, 2016 (CN) .......................... 201610614017.5

(51) Int. Cl.
| | |
|---|---|
| *A61K 31/497* | (2006.01) |
| *A61P 9/12* | (2006.01) |
| *A61K 9/00* | (2006.01) |
| *A61K 9/20* | (2006.01) |

(52) U.S. Cl.
CPC .......... *A61K 31/497* (2013.01); *A61K 9/0053* (2013.01); *A61K 9/2013* (2013.01); *A61K 9/2018* (2013.01); *A61K 9/2054* (2013.01); *A61P 9/12* (2018.01)

(58) Field of Classification Search
CPC ...... A61K 31/497; A61K 31/42; A61K 31/45; A61K 31/501; A61K 9/0053; A61K 9/2013; A61K 9/2018; A61K 9/2054; A61P 9/00; A61P 9/12
See application file for complete search history.

(56) References Cited

U.S. PATENT DOCUMENTS

| | | | | |
|---|---|---|---|---|
| 8,632,819 B2 * | 1/2014 | Thoorens | ............. | A61K 9/2009 424/499 |
| 9,708,303 B2 * | 7/2017 | Zeller | .................. | C07D 405/06 |
| 2019/0177312 A1 * | 6/2019 | Lei | ............................ | A61P 9/12 |

FOREIGN PATENT DOCUMENTS

| | | |
|---|---|---|
| CN | 103709154 A | 4/2014 |
| WO | WO-2014102628 A1 * | 7/2014 ........... A61K 9/4833 |

OTHER PUBLICATIONS

Bi, Dianzhou. Pharmaceutics, the fourth edition, People's Medical Publishing House, Nov. 30, 1999, pp. 316-325.

* cited by examiner

*Primary Examiner* — Jean P Cornet
(74) *Attorney, Agent, or Firm* — Novick, Kim & Lee, PLLC; Allen Xue

(57) ABSTRACT

The invention discloses an oral solid preparation containing any one, or a mixture of two or more of crystalline form I, II, III, and IV of the compound represented by formula (A). The oral solid preparation of the present invention disintegrates rapidly, increasing dissolution rate thereof, thereby improving bioavailability. In particular, it is possible to solve the problem that an active material (active ingredient), which is high hygroscopic and becomes sticky after moisture absorption, can not be effectively disintegrated by conventional disintegrants. The present invention further relates to a use of the oral solid preparation in preparing an angiotensin II receptor antagonist or a use thereof in preparing medicine for preventing and/or treating hypertension, chronic heart failure and diabetic nephropathy.

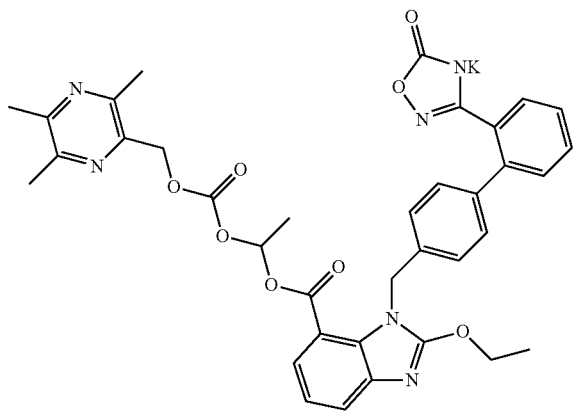

(A)

14 Claims, 7 Drawing Sheets

ORAL SOLID PREPARATION AND USE THEREOF

TECHNICAL FIELD

Embodiments of the present disclosure relate to the field of pharmaceutical preparations, and specifically relate to an oral solid preparation and the use thereof.

BACKGROUND

In general, the rate of absorption of an oral solid preparation depends on the rate at which the active substance (active ingredient) is dissolved (released) from the solid preparation, while the rate of dissolution (release) of the active ingredient often depends on the rate of disintegration of the solid preparation. In conclusion, it can be considered in general that the rate of disintegration of an oral solid preparation is a determining step of the absorption rate of the active ingredient by the body. Due to good water absorption and swelling properties of most disintegrants, adding a disintegrant to an oral solid preparation facilitates eliminating or destroying the binding force caused by an adhesive or high compression, thus promoting dissolution and absorption of the active ingredient, while rapidly fragmented into fine particulate matter in the dissolution medium, and thereby exerting a therapeutic effect. The disintegration mechanism of the disintegrant is mainly based capillary action and swelling property. Specifically, the disintegrant forms capillary channels which are easy to wet in an oral solid preparation. Accordingly, when a solid preparation is placed in a dissolution medium, the dissolution medium rapidly enters the solid preparation through the capillaries, making the entire solid preparation wetted, so that the disintegration of the oral solid formulation undergoes a wetting, siphoning, swelling and breaking process.

Commonly used disintegrants are dry starch, sodium carboxymethyl starch, low-substituted hydroxypropyl cellulose, crospovidone, croscarmellose sodium (CMC-Na), and the like, which promote the disintegration of a solid preparation mainly through effects of capillary action and swelling property. However, there exist some active substances with high hygroscopicity, which become sticky after moisture absorption and are thereby unable to be effectively disintegrated by any conventional disintegrant, resulting in poor dissolution and release properties of them.

Hypertension is the most common cardiovascular disease and is also a major risk factor leading to increased morbidity and mortality of congestive heart failure, stroke, coronary heart disease, renal failure, and aortic aneurysms. Antihypertensive drugs play an important role in the treatment and prevention of hypertension. With the deepening of the understanding of the pathogenesis of hypertension, many antihypertensive drugs with better curative effects, such as diuretics, β-blockers, calcium channel antagonists, angiotensin converting enzyme inhibitors (ACEI, prils), Angiotensin II AT1 receptor antagonist (ARB, sartans), have been continuously discovered and successfully applied in clinical practice. After years of clinical practice, it has been confirmed that the sartans of the AT1 receptor antagonist, due to their stable antihypertensive effect, good curative effect, long duration of action, good patient tolerance as well as many advantages especially in preventing stroke, delaying diabetes and non-diabetic nephropathy, improving left ventricular hypertrophy and protecting target organs, without affecting bradykinin degradation and prostaglandin synthesis so as not to cause dry cough and angioedema, has become the mainstream of the global antihypertensive drug market. However, the effective ratio of sartans antihypertensive drugs is only about 50-60%, and there exists a certain degree of adverse effect of sartans. Therefore, the development of a small-dose as well as long-acting antihypertensive drug with stronger antihypertensive effect, less adverse effect and better protection of target organs has become a hot research direction.

The Chinese Patent Application (Publication No. CN103709154A) discloses a compound of formula (B) for the first time:

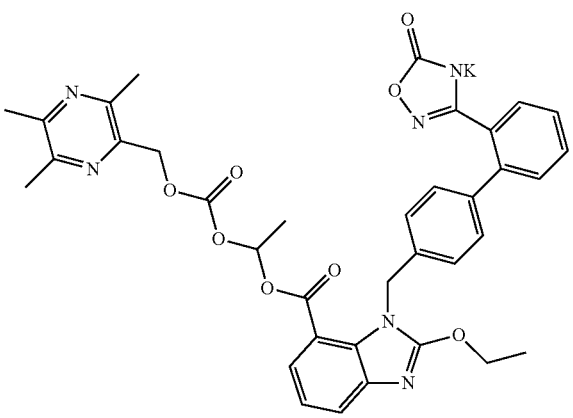

(B)

The above compound is a sartan drug which is coupled with ligustrazine and is a prodrug of angiotensin II receptor antagonist azisartan (TAK-536). The compound releases hydroxyligustrazine in vivo, thereby effectively and synergistically acting with azilsartan to enhance antihypertensive effects, produce a certain heart rate lowering effect, reduce adverse reactions, and lead an ideal protective effect on the heart and kidney of patients.

A potassium salt of compound (B), represented by the compound of formula (A) as below, has been discovered by the applicant in further studies, which has better solubility, higher bioavailability, more potent and longer-lasting antihypertensive effect, more obvious and sustainable effect of lowering heart rate, higher safety, as well as desired protective effect on the heart and kidney function of patients, and can be used for preventing and/or treating hypertension, chronic heart failure, diabetic nephropathy, and the like.

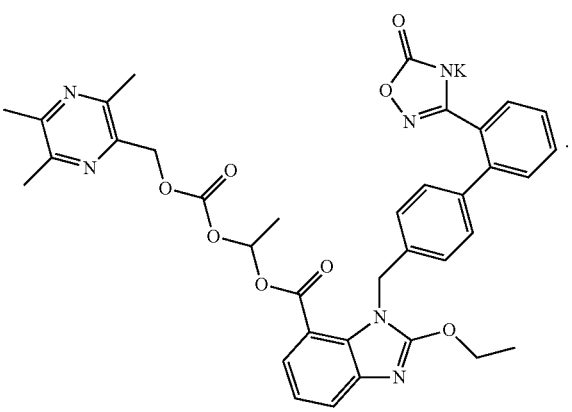

(A)

In order to improve the stability and druggability of the compound, further research is carried on by the applicant, obtaining crystalline forms I, II, III, and IV of the compound. However, during the process of preparing the above crystalline forms into an oral solid preparation, it is not effective to disintegrate the preparation using various conventional disintegrants, resulting in poor dissolution and release properties of the active ingredient. It has been found by further studies of the applicant that these crystalline forms are highly hygroscopic and become sticky after moisture absorption, so that conventional disintegrants are unable to promote disintegration, resulting in poor dissolution and release properties of the active ingredient.

SUMMARY

Embodiments of the present disclosure provides an oral solid preparation with an active ingredient, the active ingredient comprises a crystalline form of the compound of formula (A). The oral solid preparation of the present specification can rapidly disintegrate, with improved dissolution rate and bioavailability, and particularly overcome the problem referring to ineffectiveness of conventional disintegrants to disintegrate active substances (active ingredients) which have high hygroscopicity and become sticky after moisture absorption.

Conventional disintegrants promote the disintegration of a solid preparation mainly relying on the effect of capillary action which introduces water into the interior of the solid preparation and swelling property of disintegrants due to water absorption which eliminates the binding force caused by an adhesive or high compression. If active substances (active ingredients) have high hygroscopicity and therefore become sticky after moisture absorption, oral solid preparations comprising the above active substances and conventional disintegrants become difficult to disintegrate. For example, the above solid preparation is unable to disintegrate and release drug under simulated gastric acid pH conditions. This is probably because the active substance (active ingredient), which has high hygroscopicity, competing with the disintegrants to absorb moisture, and becomes sticky after water absorption, interferes with swelling of the disintegrants and blocks the water access channels, thus making the conventional disintegrants difficult to exert its disintegration performance.

In an embodiment of the present disclosure, an oral solid preparation comprising an active ingredient is provided. The active ingredient comprises a crystalline form of the compound of formula (A):

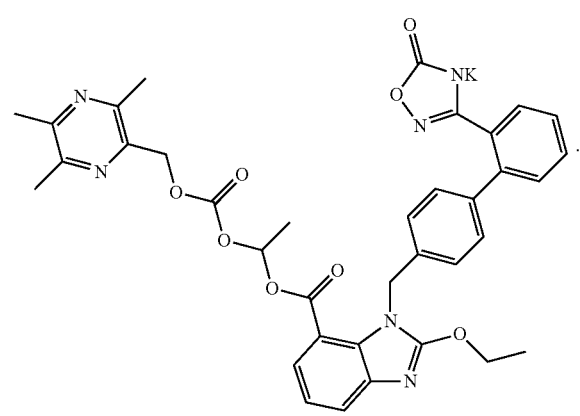

wherein, the crystalline form of the compound of formula (A) is a mixture or a mixed crystal comprising one or more selected from the group consisting of: a crystalline form I, a crystalline form II, a crystalline form III and a crystalline form IV, wherein, an X-ray powder diffraction pattern of the crystalline form I comprises characteristic peaks at diffraction angles (2-Theta) of 5.3±0.2°, 8.6±0.2°; preferably, the X-ray powder diffraction pattern of the crystalline form I further comprises characteristic peaks at diffraction angles (2-Theta) of 13.3±0.2°, 20.1±0.2°; further preferably, the X-ray powder diffraction pattern of the crystalline form I further comprises characteristic peaks at diffraction angles (2-Theta) of 6.3±0.2°, 10.6±0.2°, 26.3±0.2°; more preferably, the X-ray powder diffraction pattern of the crystalline form I further comprises characteristic peaks at diffraction angles (2-Theta) of 12.7±0.2°; most preferably, the X-ray powder diffraction pattern of the crystalline form I is substantially as shown in FIG. 1;

an X-ray powder diffraction pattern of the crystalline form II comprises characteristic peaks at diffraction angles (2-Theta) of 4.7±0.2°; preferably, the X-ray powder diffraction pattern of the crystalline form II further comprises characteristic peaks at diffraction angles (2-Theta) of 7.3±0.2°, 9.6±0.2°, 15.2±0.2°, 26.3±0.2°; further preferably, the X-ray powder diffraction pattern of the crystalline form II further comprises characteristic peaks at diffraction angles (2-Theta) of 11.8±0.2°, 24.6±0.2°; more preferably, the X-ray powder diffraction pattern of the crystalline form II further comprises characteristic peaks at diffraction angles (2-Theta) of 22.6±0.2°; most preferably, the X-ray powder diffraction pattern of the crystalline form II is substantially as shown in FIG. 2;

an X-ray powder diffraction pattern of the crystalline form III comprises characteristic peaks at diffraction angles (2-Theta) of 5.2±0.2°, 8.0±0.2°; preferably, the X-ray powder diffraction pattern of the crystalline form III further comprises characteristic peaks at diffraction angles (2-Theta) of 12.4±0.2°, 13.6±0.2°; further preferably, the X-ray powder diffraction pattern of the crystalline form III further comprises characteristic peaks at diffraction angles (2-Theta) of 19.2±0.2°; more preferably, the X-ray powder diffraction pattern of the crystalline form III further comprises characteristic peaks at diffraction angles (2-Theta) of 10.3±0.2°, 12.2±0.2°, 21.4±0.2°; most preferably, the X-ray powder diffraction pattern of the crystalline form III is substantially as shown in FIG. 3;

an X-ray powder diffraction pattern of the crystalline form IV comprises characteristic peaks at diffraction angles (2-Theta) of 7.4±0.2°, 14.7±0.2°, 16.0±0.2°; preferably, the X-ray powder diffraction pattern of the crystalline form IV further comprises characteristic peaks at diffraction angles (2-Theta) of 8.4±0.2°, 22.6±0.2°, 23.2±0.2°, 29.7±0.2°; more preferably, the X-ray powder diffraction pattern of the crystalline form IV further comprise characteristic peaks at diffraction angles (2-Theta) of 24.0±0.2°; most preferably, the X-ray powder diffraction pattern of the crystalline form IV is substantially as shown in FIG. 4.

In an embodiment of the present disclosure, for example, a DSC spectrum of the crystalline form I shows a melting temperature at 184±5° C.; a DSC spectrum of the crystalline form II shows a melting temperature at 145±5° C.; a DSC spectrum of the crystalline form III shows a melting temperature at 187±5° C.; a DSC spectrum of the crystalline form IV shows a melting temperature at 145±5° C.

In an embodiment of the present disclosure, for example, the TGA spectrum of the crystalline form I shows a decomposition temperature at 180±5° C.; the TGA spectrum of the crystalline form II shows a decomposition temperature at 148±5° C.; the TGA spectrum of the crystalline form III shows a decomposition temperature at 183±5° C.; the TGA spectrum of the crystalline form IV shows a decomposition temperature at 149±5° C.

In an embodiment of the present disclosure, for example, the crystalline form I has a DSC-TGA spectrum substantially as shown in FIG. 10; the crystalline form II has a DSC-TGA spectrum substantially as shown in FIG. 11; the crystalline form III has a DSC-TGA spectrum substantially as shown in FIG. 12; the crystalline form IV has a DSC-TGA spectrum substantially as shown in FIG. 13.

According to an embodiment of the present disclosure, the crystalline form of the compound of formula (A) may be selected from one of the crystalline forms I, II, III, IV, or a mixture or a mixed crystal of two or more of the crystalline forms I, II, III, IV in any ratio.

In an embodiment of the present disclosure, for example, a composition or a mixture comprising the crystalline forms I and II in any ratio is provided. In an embodiment of the present disclosure, for example, a mixture of the crystalline forms I and II in any ratio is provided.

Since mutual transformation between the crystalline form I and the crystalline form II may occur under certain conditions, it will be understood by those skilled in the art that a ratio of the crystalline form I and the crystalline form II in their mixture is not particularly limited. In an embodiment of the present disclosure, for example, a weight ratio of the crystalline form I to the crystalline form II may be from 1:99 to 99:1, such as from 5:95 to 95:5. As an example, a weight ratio of the crystalline form I to the crystalline form II may be from 1:9 to 9:1, from 2:8 to 8:2, from 3:7 to 7:3, from 4:6 to 6:4 or the weight ratio may be 5:5.

An amorphous form of the compound of formula (A) has poor chemical stability, with impurities produced after placement, while the chemical properties of crystalline forms I, II, III and IV are stable, with significantly less impurities produced after placement than the amorphous form. Among the four crystalline forms, the crystalline form IV is relatively unstable and will transform to the crystalline form I while drying at room temperature. The crystalline form II is relatively stable under high temperature, high humidity and tabletting conditions. The stability of the crystalline form I, II, and III at room temperature decreases in the following order: the crystalline form II>the crystalline form I>the crystalline form III.

An embodiment of the present disclosure provides a method for the preparation of the crystalline forms I, II, III and IV of the compound of formula (A).

The compound of formula (B) can be prepared by methods known in the art, such as those disclosed in CN 103709154 A. CN 103709154 A is incorporated herein in its entirety. The compound of formula (A) can be prepared by reacting the compound of formula (B) with a potassium salt reagent.

An embodiment of the present disclosure provides a method of preparation of the crystalline form I. The method comprises stirring a suspension of the compound of formula (A), adding an anti-solvent to the solution of the compound of formula (A), cooling the solution of the compound of formula (A), placing the compound of formula (A) in a solvent atmosphere, or stirring a suspension of the crystalline form III and/or the crystalline form IV of the compound of formula (A). For example, one or more proceedings as described below may be selected:

(1) adding a solvent to the compound of formula (A) to obtain a suspension, and then stirring to obtain the crystalline form I; preferably, the solvent is one or more selected from a mixture of ethanol and isopropyl ether, a mixture of ethanol and n-heptane, a mixture of isopropanol and n-heptane, and a mixture of tetrahydrofuran and n-heptane; more preferably, a volume ratio of the two solvents in the mixed solution is from 1:8 to 8:1, and most preferably from 1:5 to 5:1; preferably, the suspension is stirred at room temperature for 0.5 to 3 days, most preferably, the suspension is stirred at room temperature for 1-2 days;

(2) dissolving the compound of formula (A) into a good solvent to obtain a clear solution, and adding an anti-solvent while stirring to obtain the crystalline form I; preferably, the good solvent is one or more selected from the group consisting of methanol, ethanol and n-butanol, and the anti-solvent is one or more selected from the group consisting of isopropyl ether, methyl tert-butyl ether and methylcyclohexane;

(3) dissolving the compound of formula (A) in a solvent under heating to obtain a clear solution, and cooling the solution to obtain a crystalline form I; preferably, the solvent is one or more selected from the group consisting of a mixture of ethanol and isopropyl ether, a mixture of ethanol and ethyl acetate, a mixture of ethanol and methyl tert-butyl ether, a mixture of ethanol and n-heptane, a mixture of ethanol and methylcyclohexane, and a mixture of n-butanol and n-heptane; more preferably, a volume ratio of the two solvents in the mixed solution is from 1:8 to 8:1, and most preferably from 1:5 to 5:1; preferably, the heating temperature is from 40° C. to 90° C., and most preferably from 50° C. to 70° C.;

(4) placing the compound of formula (A) in a solvent atmosphere of ethanol for 1-3 days to obtain the crystalline form I; and (5) adding the crystalline form III and/or the crystalline form IV of the compound of formula (A) into a solvent to form a suspension, stirring and drying to obtain the crystalline form I; preferably, the solvent is selected from an ester solvent such as ethyl acetate, isopropyl acetate or a mixture thereof.

An embodiment of the present disclosure provides a method of preparation of the crystalline form II. The method comprises evaporating a solution of the compound of formula (A) to dryness; stirring a solution, a saturated solution, a supersaturated solution or a suspension of the compound of formula (A); adding an anti-solvent to the solution of the compound of formula (A); cooling the solution of the compound of formula (A); or placing the compound of formula (A) in a solvent atmosphere. For example, one or more proceedings as described below may be selected:

(1) dissolving the compound of formula (A) in a solvent to obtain a clear solution, evaporating the solution to dryness at room temperature to give the crystalline form II; preferably, the solvent is one or more selected from a mixture of ethanol and ethyl acetate, a mixture of acetone and ethyl acetate, a mixture of acetone and isopropyl ether, or a mixture of acetone and n-heptane; more preferably, the volume ratio of the two solvents in the mixture is from 1:8 to 8:1, and most preferably from 1:5 to 5:1;

(2) adding the compound of formula (A) to a solvent to obtain a clear solution, a saturated solution, a supersaturated solution or a suspension, and stirring to obtain the crystalline form II; preferably, the solvent is selected from isopropanol, sec-butanol, ethyl acetate, toluene, isopropyl acetate, a mixture of ethanol and ethyl acetate, a mixture of ethanol and isopropyl acetate, a mixture of ethanol and toluene, a mixture of acetone and n-heptane, and a mixture of 1,4-dioxane and n-heptane; more preferably, a volume ratio of the two solvents in the mixture is from 1:8 to 8:1, and most preferably from 1:5 to 5:1; preferably, stirring the mixture at room temperature for 10 minutes to 5 days, most preferably, stirring the mixture at room temperature for 3 hours to 3 days;

(3) dissolving the compound of formula (A) in a good solvent to obtain a clear solution, and adding an anti-solvent under stirring to obtain the crystalline form II; preferably, the good solvent is selected from methyl ethyl ketone, dimethyl sulfoxide or 1,4-dioxane, and the anti-solvent is selected from n-heptane, isopropyl ether or isopropyl acetate;

(4) dissolving the compound of formula (A) in a solvent under heating to obtain a clear solution, and cooling the solution to obtain the crystalline form II; preferably, the solvent is selected from sec-butanol, nitromethane, acetone, or tetrahydrofuran; preferably, the heating temperature is from 40° C. to 90° C., and most preferably, the heating temperature is from 50° C. to 70° C.;

(5) placing a saturated ethanol solution of the compound of the formula (A) in a solvent atmosphere of isopropyl ether or isopropyl acetate until the crystalline form II is precipitated out; and (6) placing the compound of formula (A) in a solvent atmosphere of toluene, isopropanol, tetrahydrofuran or ethyl acetate for 1-3 days to obtain the crystalline form II.

An embodiment of the present disclosure provides a method of preparation of crystalline form III. The method comprises stirring a suspension of the compound of formula (A), or placing the compound of formula (A) in a solvent atmosphere. For example, one or more proceedings as described below may be selected:

(1) adding tetrahydrofuran to the compound of the formula (A) to obtain a suspension and stirring the suspension to obtain the crystalline form III; preferably, stirring the suspension at room temperature for 12 hours to 5 days, and most preferably, stirring the suspension at room temperature for 1-3 days; and (2) placing a tetrahydrofuran saturated solution of the compound of formula (A) in a solvent atmosphere of isopropyl ether until the crystalline form III is precipitated out.

An embodiment of the present disclosure provides a method of preparation of the crystalline form IV. The method comprises adding an anti-solvent to the solution of the compound of formula (A). For example, the method comprises dissolving the compound of formula (A) in n-butanol to give a clear solution, and adding n-heptane under stirring to obtain the crystalline form IV.

An embodiment of the present disclosure provides a method of preparation of a mixture or a mixed crystal of the crystalline form I and the crystalline form II. The method comprises stirring a suspension of the crystalline form II at room temperature or at elevated temperature to crystallize. For example, one or more proceedings as described below may be selected:

(1) adding isopropyl acetate to the crystalline form II to obtain a suspension, and stirring at 50° C. to 90° C. to obtain a mixture of the crystalline form I and the crystalline form II; preferably, stirring the suspension at 50° C. to 90° C. for 3 hours to 3 days, and most preferably stirring the suspension at 60° C. to 90° C. for 5 hours to 1 day;

(2) pulverizing and sieving a wet product of the crystalline form II followed by vacuum drying at 40° C. to 60° C. (such as 50° C.), preferably for 3 hours to 3 days, for example 24h;

(3) vacuum drying a wet product of the crystalline form II at 40° C. to 60° C. (such as 50° C.) for 3 hours to 3 days followed by micronizing, preferably vacuum drying the wet product of the crystalline form II for 24 hours followed by micronizing; and (4) adding a solvent to the crystalline form II to obtain a suspension, stirring the suspension at room temperature to obtain a mixture of the crystalline form I and the crystalline form II; preferably, the solvent is selected from methyl tert-butyl ether or a mixture of ethanol and methylcyclohexane; more preferably, a volume ratio of the two solvents in the mixture is form 1:8 to 8:1, and most preferably from 1:6 to 5:1; preferably, stirring the suspension for 3 hours to 3 days, and most preferably, stirring the suspension for 1-3 days.

In an embodiment of the present disclosure, for example, the crystalline form I can also be used as a starting material for the preparation of the crystalline form II; preferably, the crystalline form I is added into an ester solvent such as ethyl acetate, isopropyl acetate or a mixture thereof to form a suspension, followed by stirring at room temperature overnight to obtain the crystalline form II.

In an embodiment of the present disclosure, for example, the crystalline form III can also be used as a starting material for the preparation of the crystalline form II; for example, the crystalline form III is added into an ester solvent such as ethyl acetate, isopropyl acetate or a mixture thereof to form a suspension, followed by stirring at room temperature overnight to obtain the crystalline form II.

In an embodiment of the present disclosure, for example, the crystalline form III can also be used as a starting material for the preparation of the crystalline form I; for example, the crystalline form III is added into an ester solvent such as ethyl acetate, isopropyl acetate or a mixture thereof to form a suspension, followed by stirring at room temperature overnight to obtain the crystalline form I.

In an embodiment of the present disclosure, for example, the crystalline form IV can also be used as a starting material for the preparation of the crystalline form I; for example, the crystalline form IV is dried overnight at room temperature to obtain the crystalline form I.

According to embodiments of the present invention, the oral solid preparation may further comprise a disintegrant, a disintegrant assistant, an excipient and a lubricant in addition to the active ingredient. Preferably, a content of the active ingredient is about 5-50% by weight, a content of the disintegrant is about 1-20% by weight, a content of the disintegrant assistant is about 0.1-35% by weight, a content of the excipient is about 20-80% by weight, a content of the lubricant is about 0.25-10% by weight, and a weight ratio of the disintegrant to the disintegrant assistant is from 10:1 to 1:10.

Further preferably, the content of the active ingredient is about 8-30% by weight, the content of the disintegrant is about 2-18% by weight, the content of the disintegrant assistant is about 0.5-30% by weight, the content of the excipient is about 30-80% by weight, the content of the lubricant is about 0.5-8% by weight, and the weight ratio of the disintegrant to the disintegrant assistant is from 8:1 to 1:8. More preferably, the content of the active ingredient is about 10-20% by weight, the content of the disintegrant is about 4-15% by weight, the content of the disintegrant assistant is about 1-25% by weight, the content of the excipient is about 50-80% by weight, the content of the lubricant is about 1-5% by weight, and the weight ratio of the disintegrant to the disintegrant assistant is from 5:1 to 1:5.

Most preferably, the content of the active ingredient is about 12-16% by weight, the content of the disintegrant is about 6-10% by weight, the content of the disintegrant assistant is about 2-5% by weight, the content of the excipient is about 65-78% by weight, and the content of the lubricant is about 2-4% by weight.

In embodiments of the present disclosure, the disintegrant can be a hygroscopic swelling type disintegrant. Preferably, the hygroscopic swelling type disintegrant is selected from at least one of the group consisting of dry starch, croscarmellose sodium, sodium carboxymethylcellulose, calcium carboxymethylcellulose, sodium carboxymethyl starch, methylcellulose, low degree substituted hydroxylpropyl cellulose, crospovidone, chitosan and microcrystalline cellulose.

In embodiments of the present disclosure, the disintegrant assistant is a soluble small molecule or a gas generating type salt. Preferably, the gas generating type salt is selected from at least one of the group consisting of: carbonate and hydrogencarbonate. More preferably, the gas generating salt is selected from at least one of the group consisting of: sodium carbonate, calcium carbonate, potassium carbonate, calcium magnesium carbonate, zinc carbonate, magnesium carbonate, ammonium carbonate, sodium glycinate carbonate, sodium sesquicarbonate, sodium hydrogencarbonate, calcium hydrogencarbonate, potassium hydrogencarbonate and ammonium hydrogencarbonate. Preferably, the soluble small molecule is selected from at least one of the group consisting of: sodium chloride, glucose, fructose and xylitol; more preferably, the soluble small molecule is selected from at least one of the group consisting of: sodium chloride and glucose.

The active ingredient of embodiments of the present invention has high hygroscopicity and becomes sticky after moisture absorption, thereby is not effectively disintegrated by any conventional disintegrant, resulting in poor dissolution and release properties. An oral solid preparation provided by embodiments of the present invention, with addition of a disintegrant assistant, due to the introduction of dissolution medium and rapidly dissolution of the soluble small molecule as a disintegrant assistant, not only forms capillary channels, but also brings internal and external osmotic pressure difference of the oral solid preparation, which accordingly leads to introduction of dissolution medium into the interior of the oral solid preparation and promotes the water-swelling disintegrant to cause disintegration of the solid preparation. Besides, a gas generating type salt selected as a disintegrant assistant, releases gas while contacting with the dissolution medium, thereby forming a space for introducing water, which on one hand promotes water swelling of the disintegrant to cause disintegration, and on the other hand generates gas pressure inside the preparation to promote disintegration of the solid preparation. The dissolution medium used herein refers to gastric juice, intestinal fluid, simulated gastric juice, or simulated intestinal fluid.

In embodiments of the present disclosure, the excipient is not particularly limited. Preferably, the excipient is selected from at least one of the group consisting of: starch, lactose, mannitol, cellulose lactose, microcrystalline cellulose, calcium hydrogen phosphate and mannitol-starch complex.

In embodiments of the present disclosure, the lubricant is not particularly limited. Preferably, the lubricant is selected from at least one of the group consisting of: talcum powder, magnesium stearate, calcium stearate, colloidal silica, hydrated silica, sodium octadecyl fumarate, polyethylene glycol, sodium stearyl fumarate, glyceryl monostearate and hydrogenated vegetable oil.

The oral solid preparation of embodiments of the present invention may further comprise a binder and/or a diluent.

In embodiments of the present disclosure, the binder is not particularly limited. Preferably, the binder is selected from at least one of the group consisting of: starch and derivatives thereof (including but not limited to starch, pregelatinized starch, dextrin and maltodextrin, etc.), cellulose derivatives (including but not limited to methylcellulose, carboxy methylcellulose sodium, hydroxypropylcellulose, hypromellose, ethylcellulose and microcrystalline cellulose, etc.), natural and synthetic rubbers (including but not limited to gelatin, gum arabic, locust gum and peach glue, etc.), polyethylene glycol, povidone, glycerol dibehenate, carbomer, polyvinyl alcohol, poly(meth)acrylic resin, sugar alcohols (including but not limited to sucrose, liquid glucose and maltose alcohol, etc.), corn gluten, sodium alginate and monolaurate. A suitable amount of the binder can be determined by those skilled in the art based on the active ingredient and the properties of the excipients. Generally, a content of the binder is about 0-15% by weight.

According to embodiments of the present invention, the diluent is not particularly limited. Preferably, the diluent is selected from at least one of the group consisting of lactose (for example, monohydrate, spray dried monohydrate, anhydrate, and the like), mannitol, xylitol, glucose, sucrose, sorbitol, microcrystalline cellulose, starch and calcium hydrogen phosphate dihydrate. A suitable amount of the diluent can be determined by those skilled in the art based on the properties of the active ingredient and the excipients.

The oral solid preparation of embodiments of the present invention may further optionally contain a surfactant, an antioxidant, a colorant, a flavoring agent, a preservative and/or a taste masking agent, and the like. The specific materials and suitable amounts of surfactants, antioxidants, colorants, flavoring agents, preservatives and/or taste masking agents can be determined by those skilled in the art based on the properties of the active ingredient and the excipients.

The oral solid preparation of embodiments of the present invention may be a tablet, a capsule, a powder, a granule, a dropping pill, a film or the like. Preferably, the oral solid preparation of embodiments of the present invention is a tablet. The oral solid preparation of embodiments of the present invention can be used for the preparation of an angiotensin II receptor antagonist or for the preparation of a medicament for preventing and/or treating hypertension, chronic heart failure, and diabetic nephropathy.

According to embodiments of present invention, a unit dosage form of the oral solid preparation has a total weight of about 90 mg to 600 mg and a hardness of about 3 kg to 20 kg. A content of the active ingredient is about 10 mg to 100 mg per dosage unit.

In a preferred embodiment, the active ingredient of the tablet according to embodiments of the present invention can be the crystalline form I and the crystalline form II or the mixture thereof in any ratio. According to an embodiment of the present invention, mannitol is used as an excipient, croscarmellose sodium is used as a disintegrant, sodium hydrogencarbonate is used as a disintegrant assistant, and magnesium stearate is used as a lubricant. Preferably, a content of the active ingredient is about 5-50% by weight, a content of croscarmellose sodium is about 1-20% by weight, a content of sodium hydrogencarbonate is about 0.1-35% by weight, a content of mannitol is about 20-80% by weight, a content of magnesium stearate is about 0.25-10% by weight, and a weight ratio of the disintegrant to the disintegrant assistant is from 10:1 to 1:10. Further preferably, the content of the active ingredient is about 8-30% by weight, the content of croscarmellose sodium is about 2-18% by weight, the content of sodium hydrogencarbonate is about 0.5-30% by weight, the content of mannitol is about 30-80% by weight, and the content of magnesium stearate is about 0.5-8% by weight, and the weight ratio of the disintegrant to the disintegrant assistant is from 8:1 to 1:8. More preferably, the content of the active ingredient is about 10-20% by weight, the content of croscarmellose sodium is about 4-15% by weight, the content of sodium hydrogencarbonate is about 1-25% by weight, the content of mannitol is about 50-80% by weight, the content of magnesium stearate is about 1-5% by weight, and the weight ratio of the disintegrant to the disintegrant assistant is from 5:1 to 1:5. Most preferably, the content of the active ingredient is about 12-16% by weight, the content of croscarmellose sodium is about 6-10% by weight, the content of sodium hydrogencarbonate is about 2-5% by weight, the content of mannitol is about 65-78% by weight, and the content of magnesium stearate is about 2-4% by weight.

Alternatively, the pharmaceutical composition of embodiments of the present invention may further comprise other active ingredients, such as other active ingredients for preventing and/or treating hypertension, like calcium ion antagonists (dihydropyridines, aralkylamines, phenylthiazides and triphenyl piperazines).

A process for preparing the above mentioned oral solid preparation is also provided in embodiments of the present invention, which comprises mixing the active ingredient with the other above mentioned components.

According to embodiments of the present invention, the preparation of the oral solid preparation can be carried out by a powder tabletting method, a wet granulation method or a dry granulation method.

According to embodiments of the present invention, use of the above mentioned oral solid preparation or tablet for the preparation of an angiotensin II receptor antagonist, or for the preparation of a medicament for preventing and/or treating hypertension, chronic heart failure, diabetic nephropathy is also provided.

According to embodiments of the present invention, use of the above mentioned oral solid preparation or tablet as an angiotensin II receptor antagonist or for the prevention and/or treatment of hypertension, chronic heart failure, diabetic nephropathy is also provided.

A composite disintegrant system for oral solid preparations, comprising a disintegrant and a disintegrant assistant is provided. Preferably, the composite disintegrant system for oral solid preparations consists of a disintegrant and a disintegrant assistant.

Wherein, definitions of the disintegrant and the disintegrant assistant are as described above.

According to embodiments of the present invention, preferably, a weight ratio of the disintegrant to the disintegrant assistant is from 10:1 to 1:10, more preferably from 8:1 to 1:8, and most preferably from 5:1 to 1:5.

According to embodiments of the present invention, the disintegrant assistant is an assistant agent capable of facilitating disintegrate an active material (active ingredient) which is highly hygroscopic and becomes sticky after moisture absorption. It is found that this kind of active material (which cannot be effectively disintegrated using any conventional disintegrant) can be disintegrated by addition of the soluble small molecule or the gas generating type salt, which is accordingly defined as a disintegrant assistant herein.

According to embodiments of the present invention, the composite disintegrant system may also be referred to as a composite disintegrant composition or a composite disintegrant. The composite disintegrant system of embodiments of the present invention when used to formulated an oral solid preparation, due to the introduction of dissolution medium and rapidly dissolution of the soluble small molecule as a disintegrant assistant, not only forms capillary channels, but also brings internal and external osmotic pressure difference of the oral solid preparation, which accordingly leads to introduction of dissolution medium into the interior of the oral solid preparation and promotes the water-swelling disintegrant to cause disintegration of the solid preparation. Besides, the gas generating type salt selected as a disintegrant assistant, releases gas while contacting with the dissolution medium, thereby forming a space for introducing water, which on one hand promotes water swelling of the disintegrant to cause disintegration, and on the other hand generates gas pressure inside the preparation to promote disintegration of the solid preparation. The dissolution medium used herein refers to gastric juice, intestinal fluid, simulated gastric juice, or simulated intestinal fluid.

Therefore, the composite disintegrant system provided by embodiments of the present invention is particularly suitable for an active ingredient which cannot be effectively disintegrated by any conventional disintegrant, for example, an active ingredient which is highly hygroscopic and becomes sticky after moisture absorption, including but not limited to above mentioned crystalline forms of the compound of formula (A).

Several beneficial effects can be obtained by the present disclosure, including:

1) The composite disintegrant system of embodiments of the present invention can effectively promote the collapse of the solid preparation as well as the drug release even if a large viscosity is produced by the contact of the active substance (active ingredient) with water (in which case the solid preparation cannot be disintegrated using conventional disintegrants).

2) The composite disintegrant system of embodiments of the present invention enables rapid disintegration and release of the active ingredient, thereby improving the bioavailability by only using an acidic environment, without additional acids.

3) By adding the soluble small molecule or the gas generating type salt, effective disintegration of an active substance (active ingredient) which is highly hygroscopic and becomes sticky after moisture absorption is achieved in embodiments of the present invention, thereby promoting the release of the active ingredient and improving bioavailability.

4) The solid preparation of the present invention can be used for embodiments of the prevention and/or treatment of hypertension, chronic heart failure, and diabetic nephropathy.

5) The solid preparation of embodiments of the present invention is administered by an oral route, which is convenient to use.

6) The composite disintegrant system of embodiments of the present invention can improve the drug-forming properties of the active ingredient and patient compliance.

Definitions

The term "crystalline form" means crystal structures in which a compound can crystallize in different crystal packing arrangements of its molecular and/or ion, all of which have the same elemental composition.

The term "amorphous form" refers to a noncrystalline solid state form of a molecular and/or ion, which does not show a defined X-ray powder diffraction pattern with a clear maximum.

The term "X-ray powder diffraction pattern substantially as shown in figure" or "having characteristic peaks at diffraction angles (2-Theta) substantially as shown in Figure in a X-ray powder diffraction pattern" means at least 50%, or at least 60%, or at least 70%, or at least 80%, or at least 90%, or at least 95%, or at least 99% of the main characteristic peaks shown in the X-ray powder diffraction pattern appear in the X-ray powder diffraction pattern; wherein the main characteristic peaks refers to those with relative intensity greater than 10%, and preferably greater than 30%, using the highest peak as the reference (the relative intensity of the highest peak is specified as 100%).

DETAILED DESCRIPTION

Embodiments of the present invention will be further described in detail below with reference to specific embodiments. Those skilled in the art can learn from the contents of this document and appropriately change the process parameters. It is to be noted that all such alternatives and modifications are considered to be included within the scope of the present invention. The products of the present invention have been described in terms of preferred embodiments, and the present invention can be implemented and applied without departing from the spirit and scope of the invention.

Example 1: Preparation of a Compound of Formula (A)

A compound of the formula (B) (1.0 g) was dissolved in dichloromethane (5 ml), and the mixture was stirred at room temperature to form a solution, which was then added with potassium phthalimide (0.27 g), kept for 4 h at room temperature, and cooled to −50° C., followed by filtration and rotary evaporation to obtain the compound of formula (A) (amorphous form).

Melting point: 135-145° C.

MS/HRMS m/z: 717 [M+H]$^+$; 677 [M−K]$^−$.

$^1$H-NMR (400 MHz, DMSO-d6) δ: 1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

Figure 5:
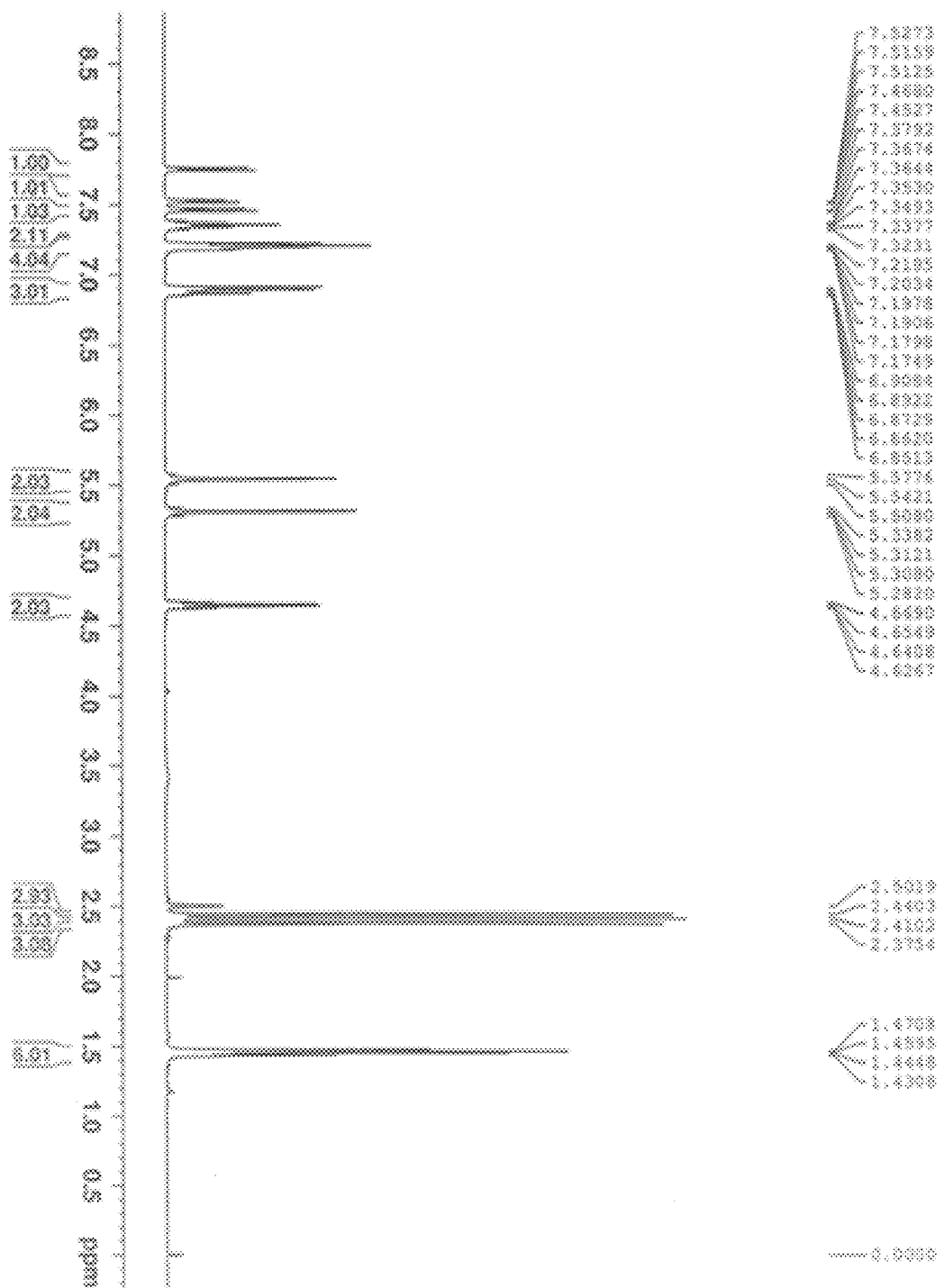
FIG. 5 is a $^1$H-NMR spectrum of the compound of formula (A)
Figure 6:
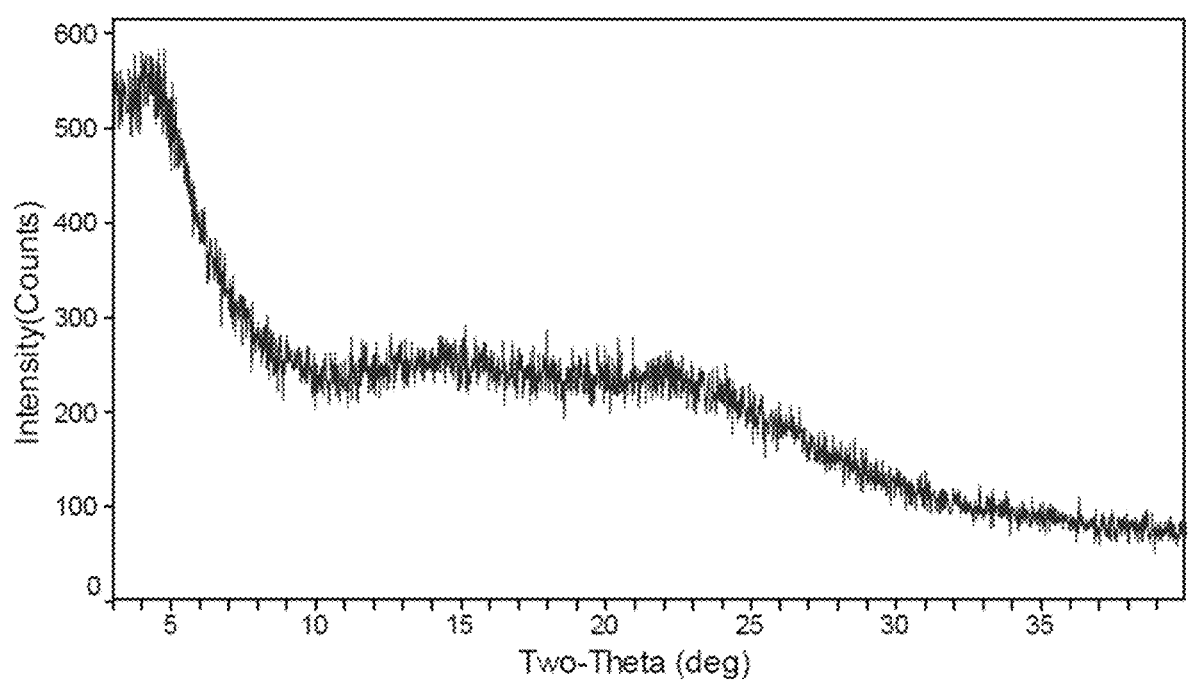
FIG. 6 is an X-ray powder diffraction pattern of the amorphous form of the compound of formula (A)

The $^1$H-NMR spectrum and the X-ray powder diffraction pattern are respectively shown in FIG. 5 and FIG. 6.

Example 2: Antihypertensive Efficacy Test of the Compound of Formula (A) in Spontaneously Hypertensive Rats 12-week-old spontaneously hypertensive rats (hereinafter referred to as SHR, purchased from Beijing Weitong Lihua Experimental Animal Technology Co., Ltd.) were anesthetized with 2.5% sodium pentobarbital for intraperitoneal injection. After that, the blood pressure sensing catheter of hypertension implant was inserted into their abdominal aorta, while the implant was fixed to the abdominal wall, and then postoperative daily care is performed after suturing.

Rats with systolic blood pressure exceeding 160 mm Hg were divided into 3 groups (control group, compound (A) group and compound (B) group), wherein each group has 8 rats. The control group was administrated 0.5% sodium carboxymethylcellulose (hereinafter referred to as CMC-Na); the compound (B) group and the compound (A) group were respectively administered the compound (B) and the compound (A), both of which were dissolved by 0.5% CMC-Na, by intragastric administration, at a dose of 1 mg/kg (calculated by the effective dose of valsartan) and a volume calculated by 4 mL/kg.

The systolic blood pressure and heart rate of SHR were compared before and after administration (the systolic blood pressure and heart rate of SHR before administration as reference value), which were detected three times at each time point with the average value recorded. The results are shown in Tables 1 and 2 below.

TABLE 1

Systolic blood pressure change at each time point before and after intragastric administration of the compound of formula (B) and compound of formula (A) (average (mmHg) ± standard error)

| Group | Before administration | 1 hour after administration | 3 hours after administration | 5 hours after administration |
|---|---|---|---|---|
| Control group | 0.0 ± 0.0 | 5.4 ± 7.1 | −3.5 ± 4.6 | 4.5 ± 4.0 |
| Compound (B) group | 0.0 ± 0.0 | −4.9 ± 4.8 | −22.0 ± 3.6* | −30.5 ± 3.5* |
| Compound (A) group | 0.0 ± 0.0 | −7.0 ± 3.4 | −34.3 ± 1.9* | −46.5 ± 2.5* |

| Group | 7 hours after administration | 10 hours after administration | 24 hours after administration |
|---|---|---|---|
| Control group | 4.1 ± 3.2 | −2.9 ± 2.3 | −2.7 ± 6.4 |
| Compound (B) group | −38.8 ± 2.3* | −33.0 ± 1.7* | −10.2 ± 2.1 |
| Compound (A) group | −49.4 ± 4.1* | −45.3 ± 3.3* | −25.9 ± 3.4* |

*$P < 0.01$ (relative to the control group)

It can be seen from the results in Table 1 that after 3 hours of administration, the systolic blood pressure of the compound (B) group or the compound (A) group is significantly decreased compared with the control group, and the drug efficacy peaks 5-7 hours after administration, and the compound (A) group is more potent with longer-lasting antihypertensive effect, compared with the compound (B) group.

TABLE 2

Heart rates change before and after oral administration of the compound of formula (B) and compound of formula (A) (average (times/minute) ± standard error)

| Group | Before administration | 1 hour after administration | 3 hours after administration | 5 hours after administration |
|---|---|---|---|---|
| Control group | 0.0 ± 0.0 | 0.14 ± 2.9 | 6.4 ± 2.8 | −0.3 ± 2.7 |
| Compound (B) group | 0.0 ± 0.0 | −3.4 ± 2.6 | −2.33 ± 2.6* | −6.5 ± 2.8* |
| Compound (A) group | 0.0 ± 0.0 | −3.6 ± 2.4 | −5.0 ± 2.5* | −10.1 ± 3.0* |

| Group | 7 hours after administration | 10 hours after administration | 24 hours after administration |
|---|---|---|---|
| Control group | −0.1 ± 2.9 | −2.5 ± 2.5 | 4.3 ± 2.8 |
| Compound (B) group | −6.2 ± 3.0* | −12.3 ± 2.8* | −6.7 ± 2.6* |
| Compound (A) group | −17.5 ± 3.0* | −25.4 ± 2.4* | −28.6 ± 8* |

*$P < 0.05$ (relative to the one-way ANOVA of the control group).

It can be seen from the results in Table 2 that the compound (A) group is more potent with longer-lasting of lowering heart rate compared with the compound (B) group.

Example 3: Preparation of Crystalline Form I of the Compound (A)

Figure 1:
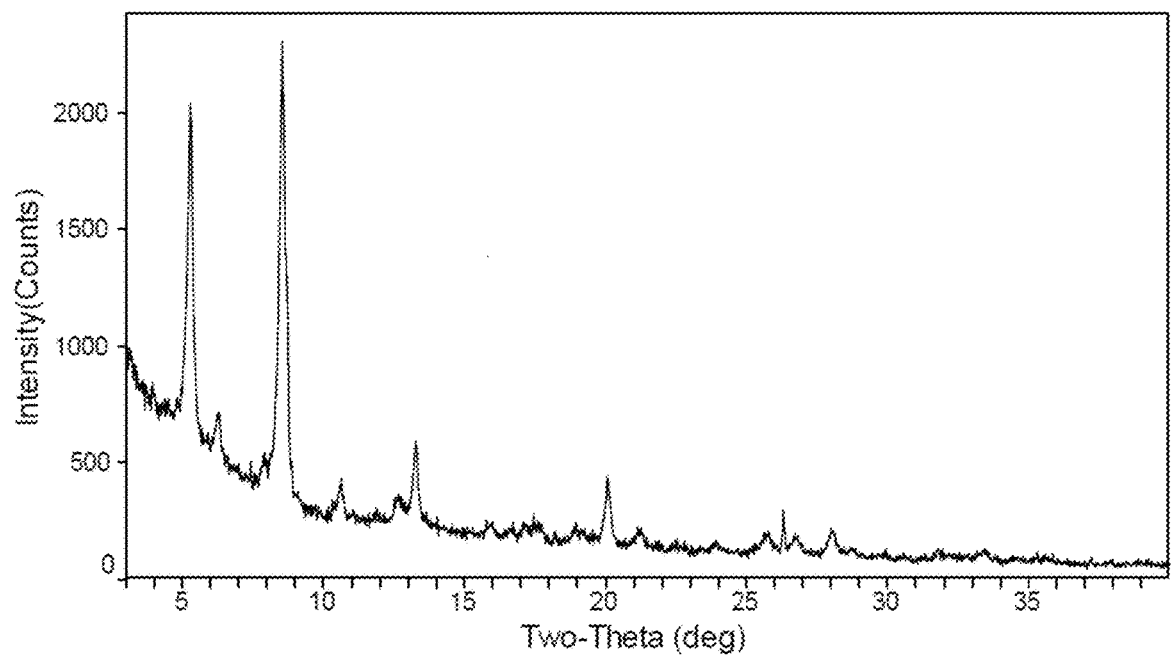
FIG. 1 is an X-ray powder diffraction pattern of the crystalline form I.

(1) 15 mg compound of formula (A) was added with a mixed solution of 0.2 ml of ethanol/isopropyl ether (1:5 v/v) to obtain a suspension, which was stirred at room temperature for 1 day, filtered, and dried to give the crystalline form I. The XRD detection pattern is shown in FIG. 1; DSC: 184° C. The crystalline form I was also prepared through the above procedures with the mixed solution replaced by ethanol and n-heptane (1:5 v/v), isopropanol and n-heptane (1:5 v/v), or tetrahydrofuran and n-heptane (1:5 v/v).

(2) 15 mg compound of formula (A) was dissolved in 0.1 ml of methanol (good solvent) to obtain a clear solution, which was added with 1.0 ml of isopropyl ether (anti-solvent) while stirring to precipitate a solid, and then stirred, filtered and dried to give the crystalline form I. The crystalline form I was also prepared through the above procedures with the solvent replaced by ethanol (good solvent)/isopropyl ether (anti-solvent), ethanol (good solvent)/methyl tert-butyl ether (anti-solvent), ethanol (good solvent)/methylcyclohexane (anti-solvent), n-butanol (good solvent)/propyl ether (anti-solvent).

(3) 10 mg compound of formula (A) was dissolved in a mixed solution of ethanol and isopropyl ether (0.2 ml: 0.5 ml) at 60° C. to obtain a clear solution, which was cooled to give the crystalline form I. The crystalline form I was also prepared through the above procedures with the mixed solution replaced by ethanol and ethyl acetate (0.1 ml: 0.5 ml), ethanol and methyl tert-butyl ether (0.2 ml: 0.5 ml), ethanol/n-heptane (0.2 ml: 0.5 ml), ethanol and methylcyclohexane (0.2 ml: 0.5 ml), or n-butanol and n-heptane (0.2 ml: 0.5 ml).

(4) 8 mg compound of formula (A) was placed in a solvent atmosphere of ethanol (that is, placed in a large vessel containing ethanol) for 1 day, and dried to obtain the crystalline form I.

(5) 0.2 ml of ethyl acetate was added to 15 mg crystalline form III of the compound of formula (A) to form a suspension, stirred overnight, and dried to give the crystalline form I.

(6) 0.2 ml of ethyl acetate was added to 15 mg crystalline form IV of the compound of formula (A) to form a suspension, stirred overnight, and dried at room temperature to obtain the crystalline form I.

Example 4: Preparation of Crystalline Form II of the Compound (A)

Figure 2:
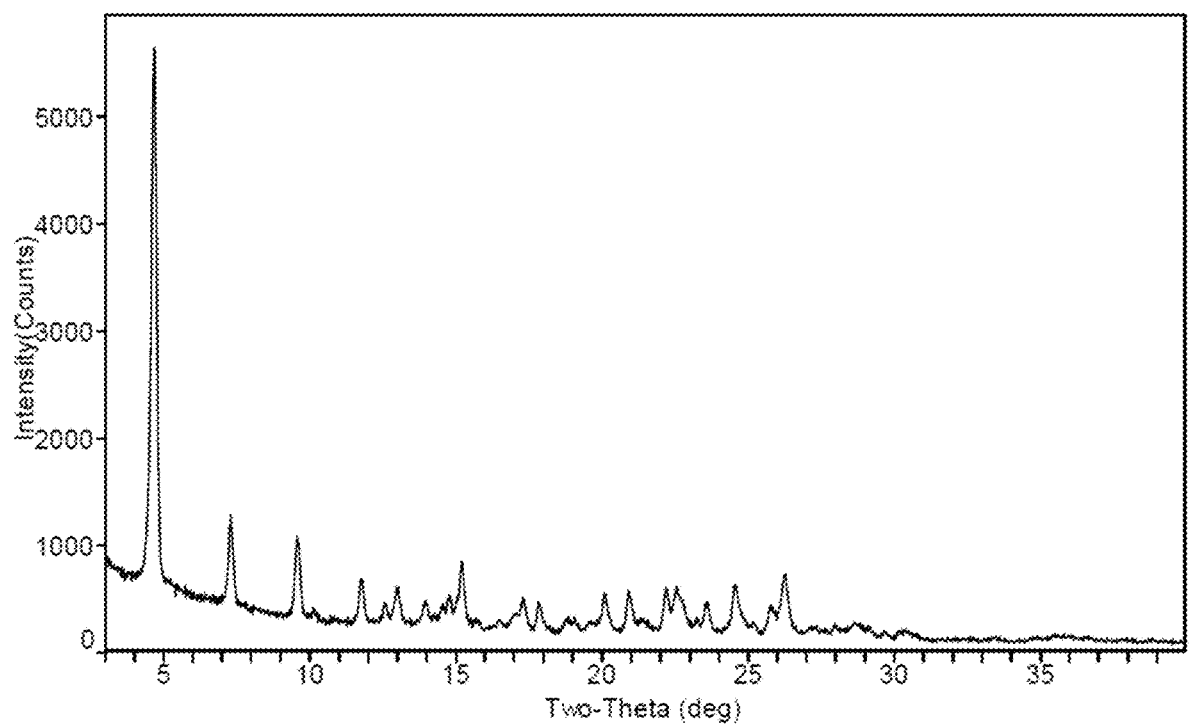
FIG. 2 is an X-ray powder diffraction pattern of the crystalline form II.

(1) 10 ml of ethyl acetate was added to 1.1 g compound of formula (A) to obtain a clear solution, which was stirred at room temperature for 3 hours, filter and dried to obtain 0.88 g product. The XRD detection spectrum of the obtained crystalline form II is shown in FIG. 2; DSC: 145.4° C. It was found that with gradually reduced ethyl acetate, the crystalline form II can be obtained through stirring of a saturated solution, a supersaturated solution and a suspension of the compound of formula (A).

The crystalline form II was also prepared by the above procedures with the solvent (ethyl acetate) replaced by isopropanol, sec-butanol, isopropyl acetate, toluene, a mixture of ethanol and ethyl acetate (1:5 v/v), a mixture of ethanol and isopropyl acetate (1:5 v/v), a mixture of ethanol and toluene (1:5 v/v), a mixture of acetone and n-heptane (1:5 v/v), or a mixture of 1,4-dioxane and n-heptane (1:5 v/v).

(2) 5 mg compound of formula (A) was dissolved in a mixed solution of ethanol and ethyl acetate (0.2 ml: 0.5 ml) to obtain a clear solution, which was evaporated to dryness at room temperature to obtain the crystalline form II. The crystalline form II was also prepared by the above procedures with the mixed solution replaced by acetone and ethyl acetate (1.0 ml: 0.5 ml), acetone and isopropyl ether (2.0 ml: 0.5 ml), or acetone and n-heptane (2.0 ml: 0.5 ml).

(3) 15 mg compound of formula (A) was dissolved in 0.8 ml butanone (good solvent) to obtain a clear solution, and added with 4.0 ml n-heptane (anti-solvent) under stirring to precipitate a solid, which was filtered and dried to give the crystalline form II. The crystalline form II was also prepared by the above procedures with the solvent replaced by methyl ethyl ketone (good solvent) and isopropyl ether (anti-solvent), dimethyl sulfoxide (good solvent) and isopropyl acetate (anti-solvent), or 1,4-dioxane (good solvent) and isopropyl ether (anti-solvent).

(4) 10 mg compound of formula (A) was dissolved in sec-butanol at 60° C. to obtain a clear solution, which was cooled to give the crystalline form II. The crystalline form II was also prepared by the above procedures with the solvent replaced by nitromethane, acetone or tetrahydrofuran.

(5) 5 mg compound of formula (A) was dissolved in an appropriate amount of ethanol to obtain a saturated solution, which was dispersed in a solvent atmosphere of isopropyl ether (that is, placed in large vessel containing isopropyl ether) until precipitating a solid and then filtered and dried to obtain the crystalline form II. The crystalline form II was also obtained through the above procedures by replacing isopropyl ether with isopropyl acetate.

(6) 8 mg compound of formula (A) was placed in a solvent atmosphere of toluene (that is, placed in a large vessel containing toluene) for 3 days, and dried to obtain the crystalline form II. The crystalline form II was also obtained through the above procedures by replacing toluene with isopropanol, tetrahydrofuran or ethyl acetate.

Example 5: Preparation of Crystalline Form III f Compound (A)

Figure 3:
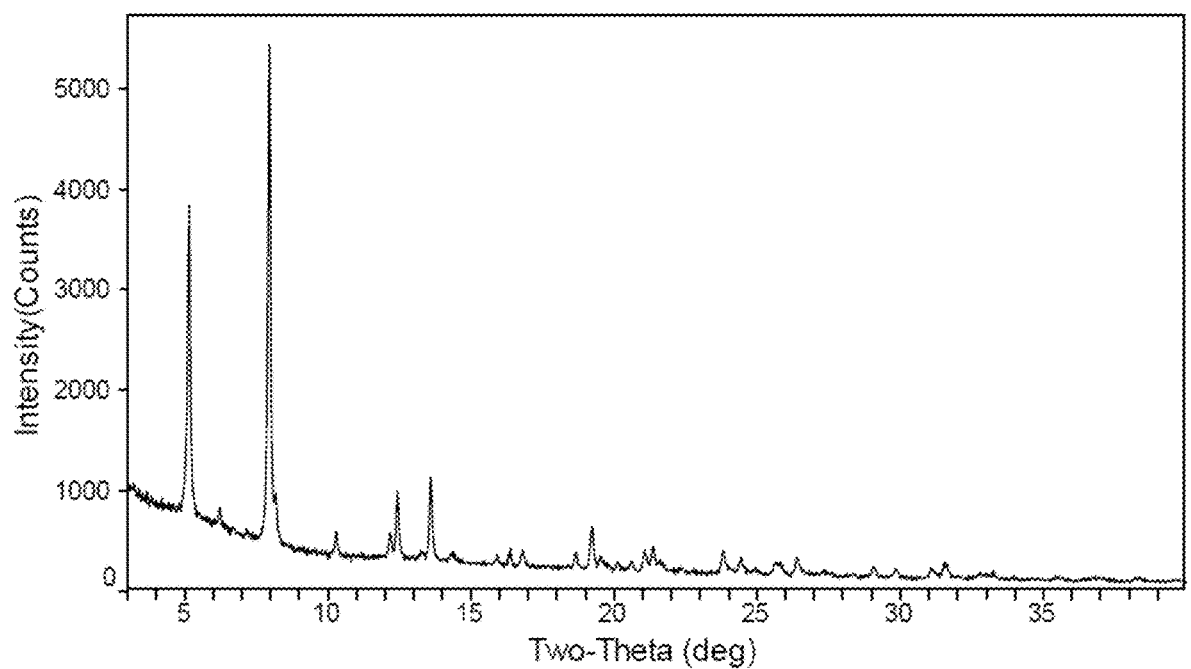
FIG. 3 is an X-ray powder diffraction pattern of the crystalline form III.

(1) 1.0 ml of tetrahydrofuran was added to 100 mg compound of formula (A) to obtain a suspension, which was stirred at room temperature for 1 day, filtered, and dried. The XRD detection spectrum of the obtained crystalline form III is shown in FIG. 3; DSC: 187.3° C.

(2) 5 mg compound of formula (A) was dissolved in an appropriate amount of tetrahydrofuran to obtain a saturated solution, which was placed in a solvent atmosphere of isopropyl ether (that is, placed in a large vessel containing isopropyl ether) to stand until precipitating a solid, and then filtered and dried to obtain the crystalline form III.

Example 6: Preparation of Crystalline Form IV of Compound (A)

Figure 4:
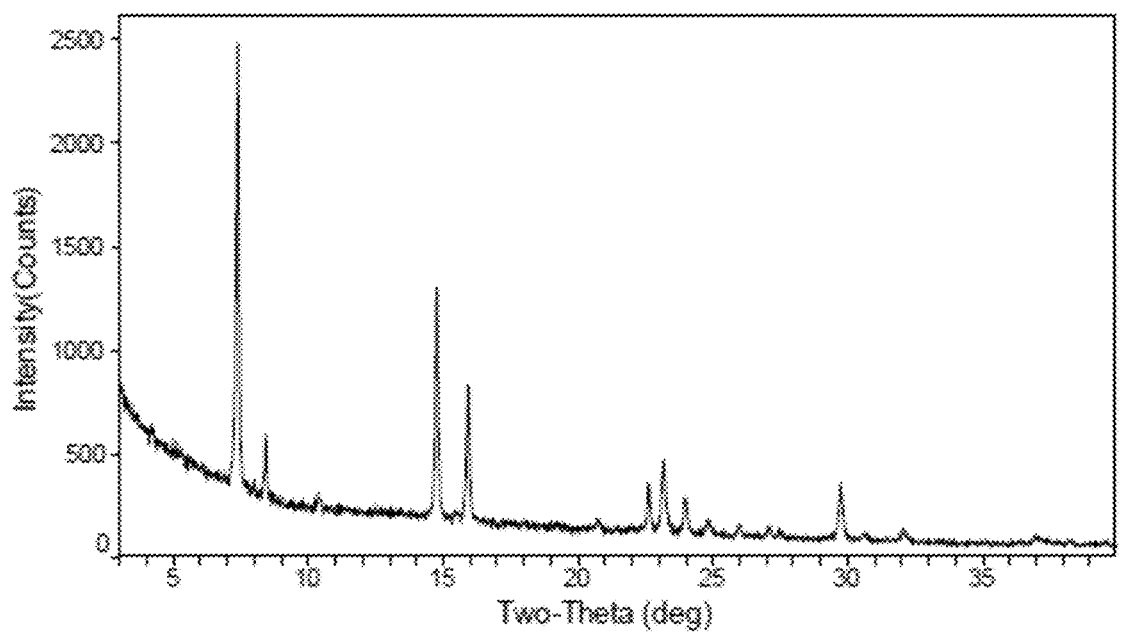
FIG. 4 is an X-ray powder diffraction pattern of the crystalline form IV.

50 mg compound of formula (A) was dissolved in 1.0 ml of n-butanol to obtain a clear solution, added with 5.0 ml n-heptane under stirring to precipitate a solid and filtered. The XRD detection spectrum of the obtained crystalline form IV is shown in FIG. 4; DSC melting point: 144.7° C.

Figure 7:
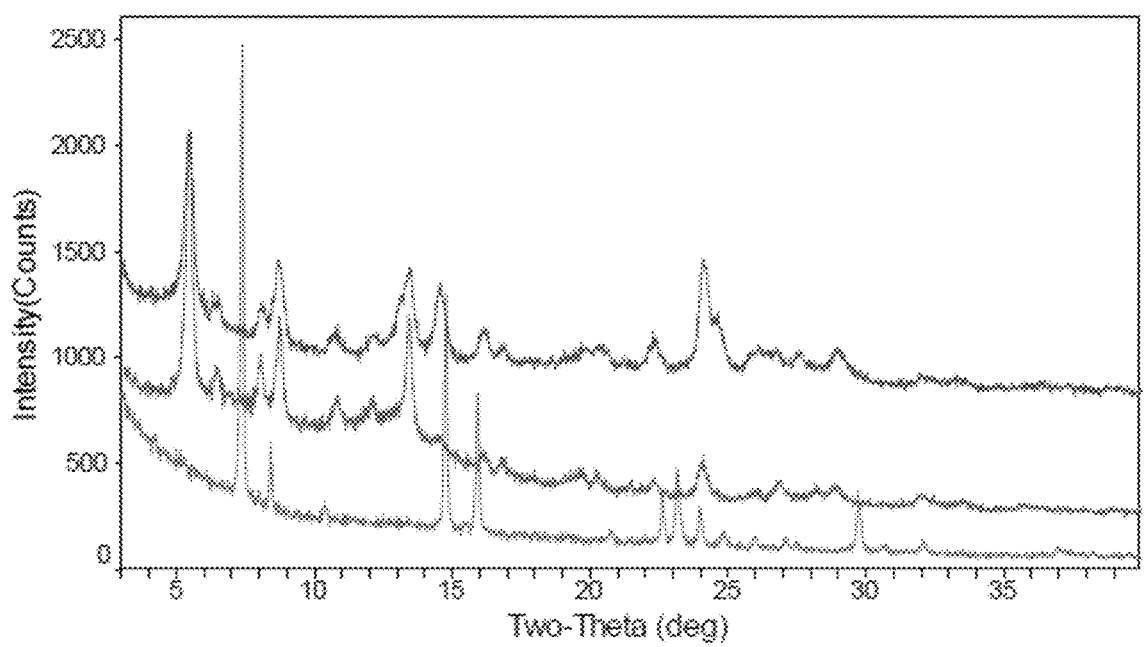
FIG. 7 is an X-ray powder diffraction pattern of the crystalline form IV before and after drying at room temperature (from top to bottom: the crystalline form I, the crystalline form IV after drying at room temperature and the crystalline form IV)

The crystalline form IV can be converted to the crystalline form I by drying at room temperature, as shown in FIG. 7.

Example 7: Preparation of a Mixture of the Crystalline Form I and the Crystalline Form II (1) 100 mg of the crystalline form II was added with 2.5 ml isopropyl acetate to obtain a suspension, which was stirred in a water bath at 80° C. for 8 hours, filtered, and dried. It is determined by X-ray detection that the crude product contains about 95% of the crystalline form I and about 5% of the crystalline form II.

(2) 100 mg wet product of the crystalline form II was pulverized, sieved, and vacuum-dried at 50° C. for 24 h. It is determined by X-ray detection that the crude product contains about 10% of the crystalline form I and about 90% of the crystalline form II.

(3) 100 mg wet product of the crystalline form II was vacuum-dried at 50° C. for 24 h followed by micronized by a micro-powder machine. It is determined by X-ray detection that the crude product contains 30% of the crystalline form I and about 70% of the crystalline form II.

(4) 15 mg of the crystalline form II was added with 0.5 ml methyl tert-butyl ether to obtain a suspension, which was stirred at room temperature for 3 days, filtered, and dried to obtain a mixture of the crystalline form I and the crystalline form II, A mixture of crystalline form I and crystalline form II is also obtained through the above procedures by replacing methyl tert-butyl ether with a mixed solution of ethanol and methylcyclohexane (1:5 v/v).

Example 8: Room Temperature Competition Test (1) Competition experiment between the crystalline form I and the crystalline form II Equivalent amounts of the crystalline form I and the crystalline form II samples were mixed well, added with 0.8 ml ethyl acetate to form a suspension, stirred overnight and detected by XRD. It is determined that the obtained product contains about 5% of the crystalline form I by comparing the XRD of the obtained product of a mixture of crystalline form I and crystalline form II in which a ratio of the crystalline form I: the crystalline form II is gradually and equally increased. In terms of the significant weakening tendency of the characteristic peaks of crystalline form I, it can be expected that the crystalline form I will be completely transformed into the crystalline form II when given sufficient time. Consequently, it turns out that the stability of the crystalline form II is better than that of the crystalline form I under room temperature.

(2) Competition experiment between the crystalline form II and the crystalline form III Equivalent amounts of the crystalline form II and the crystalline form III samples were mixed well, added with 0.2 ml ethyl acetate to form a suspension, which was stirred overnight to obtain the crystalline form II determined by XRD detection. It turns out that the crystalline form III in the mixture is completely transformed into the crystalline form II. Consequently, the stability of the crystalline form II is better than that of the crystalline form III under room temperature.

(3) Competition experiment between crystalline form I and crystalline form III

Equivalent amounts of the crystalline form I and the crystalline form III samples were mixed uniformly, added with 0.2 ml ethyl acetate to form a suspension, which was stirred overnight, to obtain the crystalline form I determined by XRD detection. It turns out that the crystalline form III in the mixture is completely transformed into the crystalline form I. Consequently, the stability of the crystalline form I is better than that of the crystalline form III under room temperature.

(4) Comparative experiment of stability between the crystalline form III and the crystalline form IV The Crystalline form III and the crystalline form IV samples were respectively dried overnight at room temperature. It turns out by XRD detection that only no more than 30% of the crystalline form III was converted to the crystalline form I. However, the crystalline form IV is completely transformed into the crystalline form I, showing poor stability. The above experiments turn out that the stability of the crystalline forms I, II and III is superior to that of the crystalline form IV at room temperature.

Example 9: Investigation of the Effect of Tabletting Processes on the Crystalline Form II Tabletting method: 50 mg of the crystalline form II was tableted under 20 kg and 25 kg pressure tabletting by a single punching machine.

Figure 8:
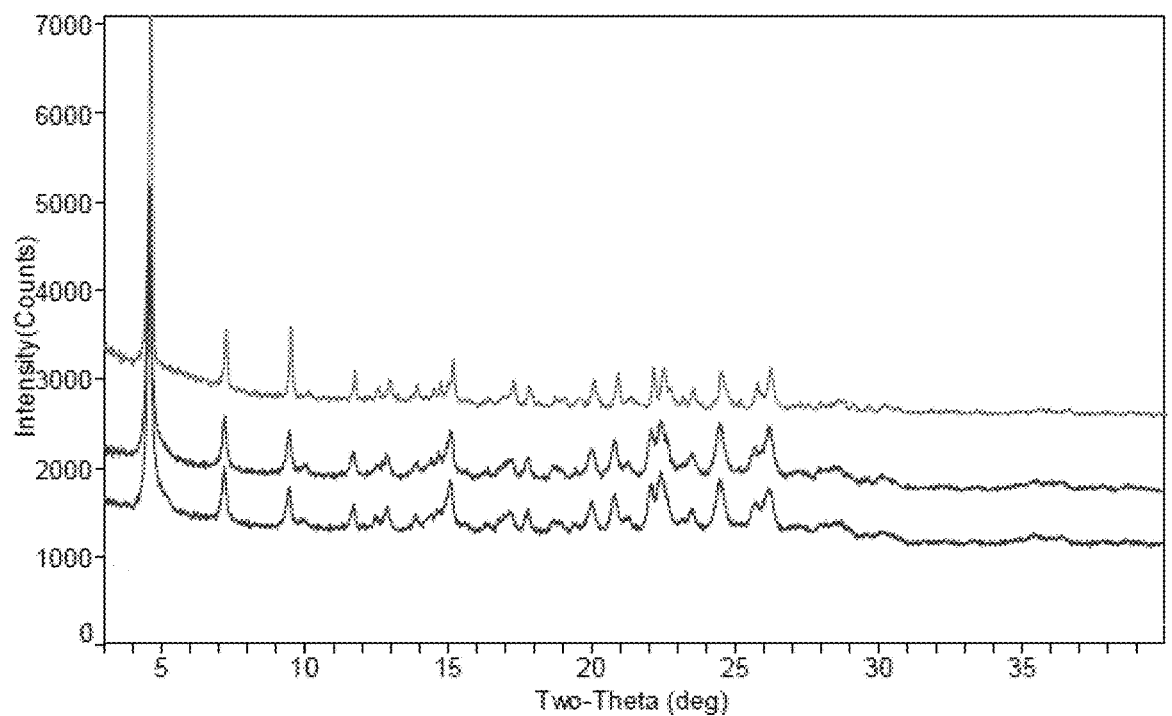
FIG. 8 is an X-ray powder diffraction pattern of the crystalline form II under tabletting conditions (from top to bottom: a crude sample, a sample after 25 kg pressure tabletting and a sample after 20 kg pressure tabletting)

The XRD of the obtained sample powder was compared with the XRD of the crude sample, the results are shown in FIG. 8 (from top to bottom: the crude sample, the sample after 25 kg pressure tabletting and the sample after 20 kg pressure tabletting). It turns out that the crystalline form II remains unchanged after tabletting.

Figure 9:
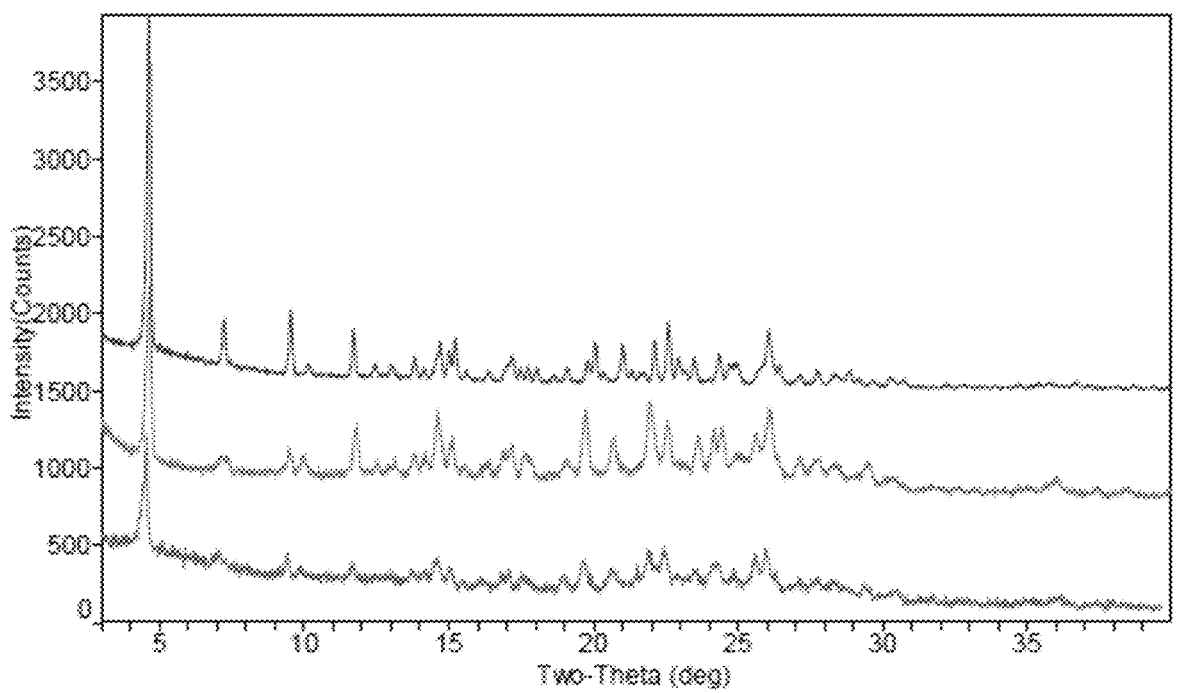
FIG. 9 is an X-ray powder diffraction pattern of crystalline form II after 10 days under high temperature and high humidity conditions (from top to bottom: the crude sample, the sample at 60° C., a sample at 85% relative humidity)
Figure 10:
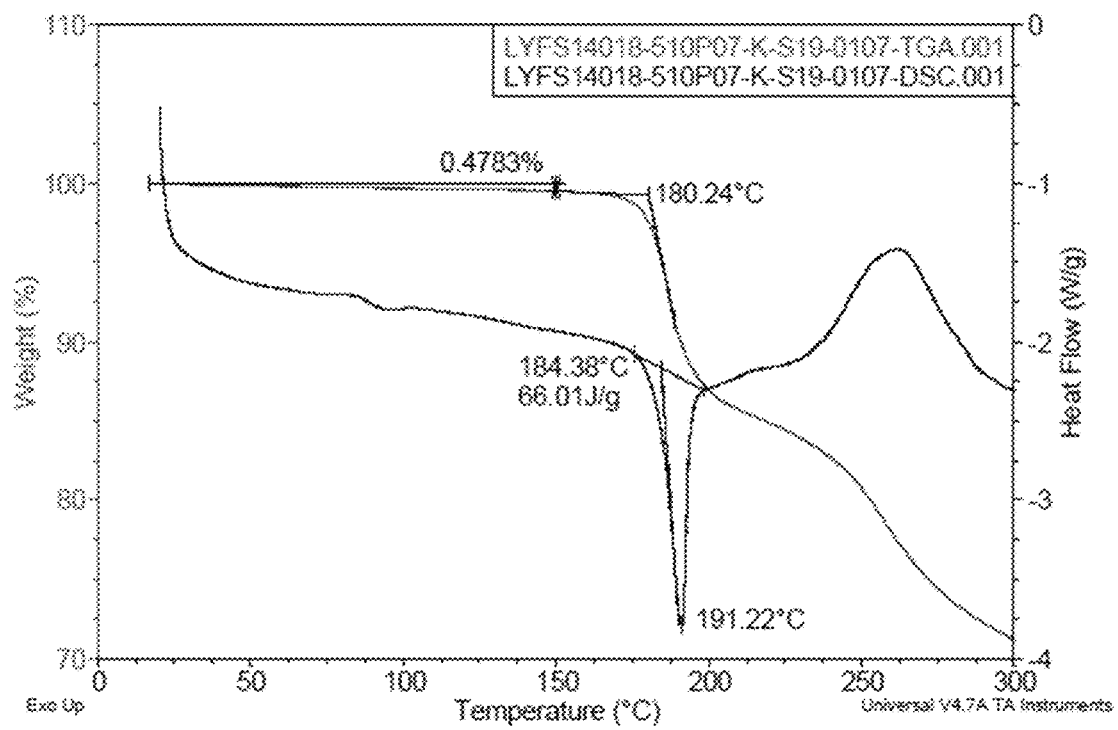
FIG. 10 is a DSC-TGA spectrum of the crystalline form I.
Figure 11:
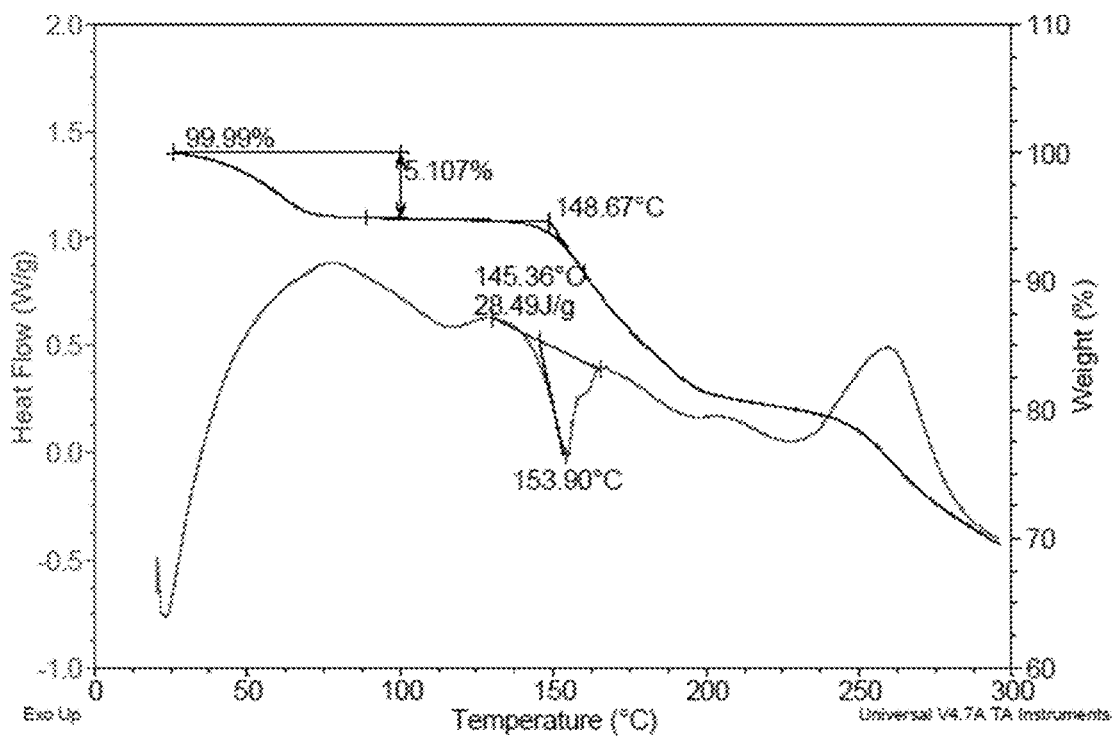
FIG. 11 is a DSC-TGA spectrum of the crystalline form II.
Figure 12:
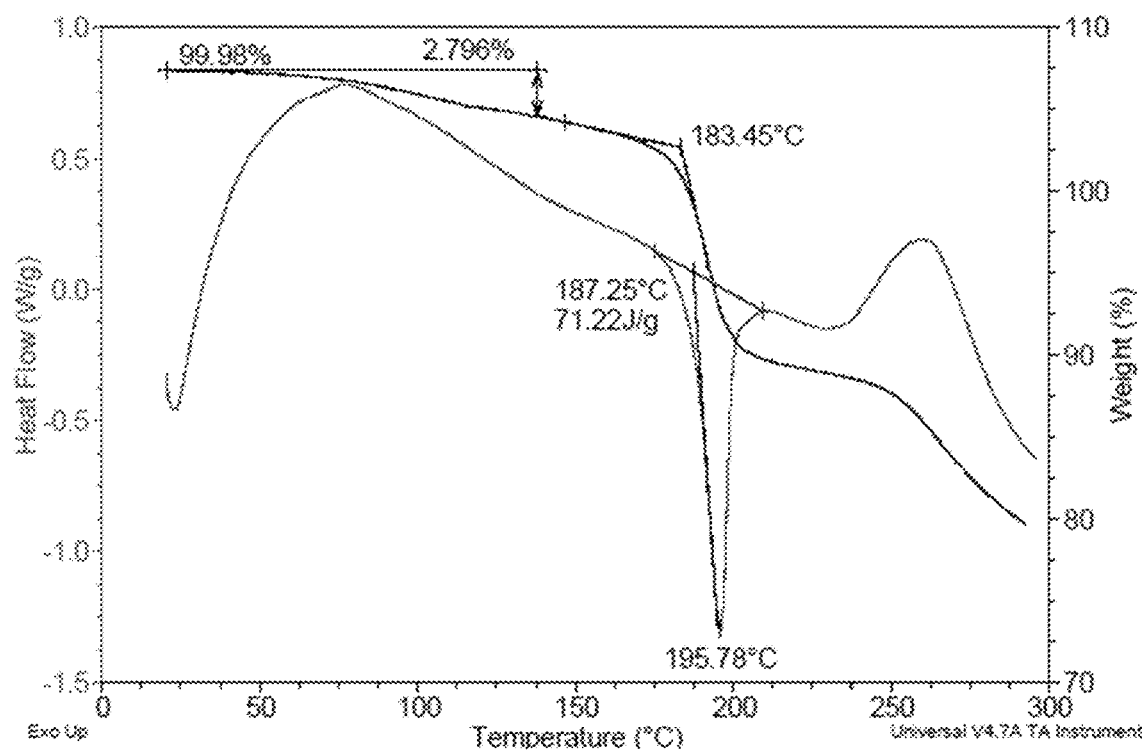
FIG. 12 is a DSC-TGA spectrum of the crystalline form III.
Figure 13:
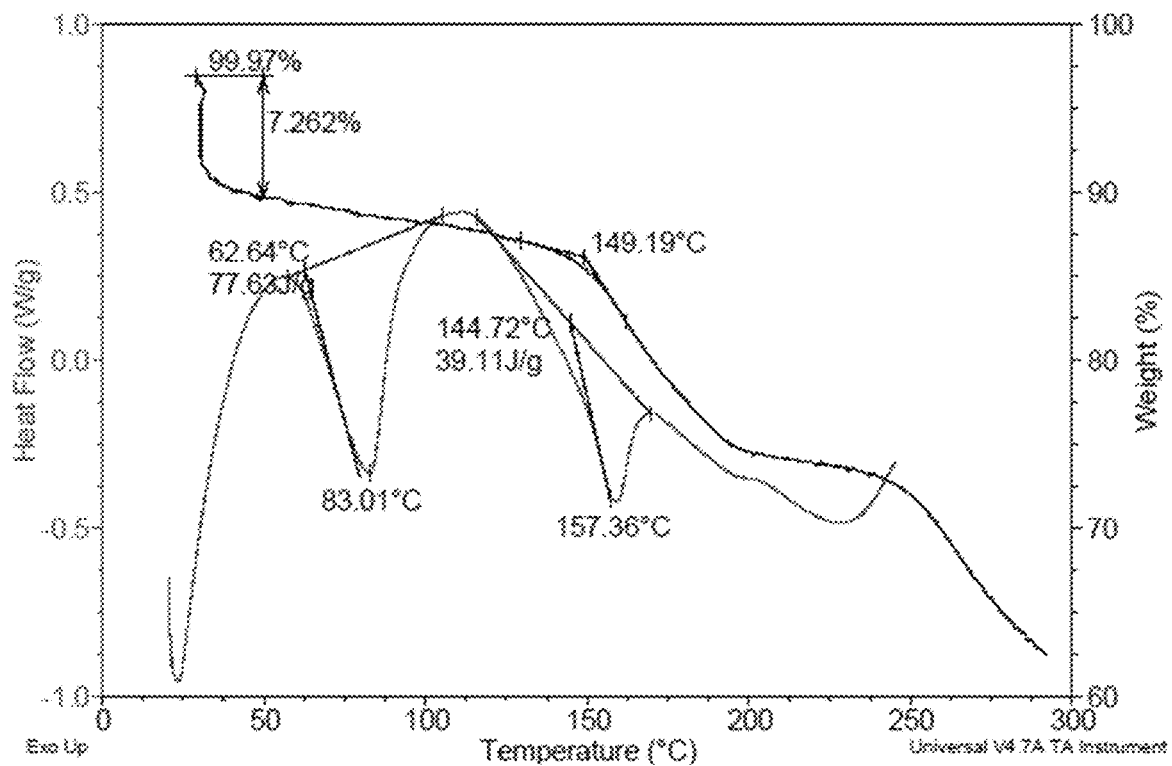
FIG. 13 is a DSC-TGA spectrum of the crystalline form IV.

Example 10: Investigating the Influences of High Temperature and High Humidity on the Crystalline Form II Two samples of 20 mg of the crystalline form II were respectively placed at 60° C. (sealed and shielded from light) and 85% relative humidity (exposed in the air at room temperature and shielded from light), detected by XRD after 10 days and compared with the XRD of the crude sample. It turns out that the crystalline form II remains unchanged as shown in FIG. 9 (from top to bottom: the crude sample, the sample at 60° C. and the sample at 85% relative humidity).

Example 11: Comparative Stability Test

The stability of an amorphous form, a mixture of the crystalline forms I and the crystal II, the crystalline form II and the crystal form III of the compound of formula (A) were investigated. Specifically, the amorphous form, the mixture of the crystalline form I and the crystalline form II (weight ratio 1:2), the crystalline form II and the crystalline form III were taken 200 mg respectively to be investigated as follows:

Packing: Polyvinyl chloride (PVC) material ziplock bag (the inner layer) was vacuumized, aluminum foil (the middle layer) was vacuumized, and aluminum foil desiccant (the outer layer) was vacuum and filled in with nitrogen;

Inspection conditions: 25° C., 60% relative humidity. The indicator was the total impurity content, which is determined by detection of samples three times at each time point with the average value recorded. The time points for sampling include 0, 1, 2, 3 and 6 months after packing. The test results are shown in Table 3 below.

TABLE 3

| | Comparative stability test | | | | |
|---|---|---|---|---|---|
| objects of | total impurity content % at different time (months) | | | | |
| investigation | 0 | 1 | 2 | 3 | 6 |
| amorphous form | 1.52 | 13.28 | — | — | — |
| crystalline form I | 1.11 | 1.62 | 2.34 | 2.49 | 3.10 |
| mixture of crystalline form I and II | 0.90 | 1.58 | 2.20 | 2.40 | 3.29 |
| crystalline form II | 1.29 | 1.43 | 1.59 | 1.82 | 1.87 |
| crystalline form III | 1.56 | 2.55 | 2.98 | 3.34 | 3.76 |

It can be seen from the results of Table 3 that the chemical stability of the crystalline form I, the crystalline form II, the crystalline form III and the mixture of the crystalline form I and the crystalline form II is better than the amorphous form. Consequently, the crystalline forms of the compound (A) are more favorable to the quality control of drugs and drug-forming properties.

Example 12: Preparation and Disintegration Experiment of an Oral Solid Preparation The tablets of preparation examples 1-11 and comparative examples 1-11 were prepared according to the following three preparation methods. The formula composition and differences in tablet hardness and tablet weight of each preparation example and each comparative example were shown in Table 4 below.

Preparation examples 1, 7, 8, 9 as well as comparative examples 1, 7, 8, 9 employed a powder tabletting method: a 60-mesh sieve was selected according to the material properties, and the materials were sieved for use (in preparation example 7 and comparative example 7, the active ingredients were sifted together with the excipients, besides, the disintegrant and the disintegrant assistant were mixed together and sieved for use; while in the other preparation examples and comparative examples, above components were sieved separately); the active ingredient, the excipient, the disintegrant, and the disintegrant assistant (which was not added in comparative examples) were poured into a three-dimensional mixer for mixing, and then added with a lubricant for final mixing; the final mixed material was tableted in a rotary tabletting machine.

A wet granulation method was employed in preparation examples 2, 4, 5, 10 as well as comparative examples 2, 4, 5, 10: a 60 mesh sieve was selected according to the material properties, and the materials were sieved for use; the active ingredient, excipient, disintegrant, and disintegrant assistant (which was not added in comparative examples) were poured into a granulator, mixed together, added with an aqueous solution of the binder (5% aqueous solution of povidone was used in preparation example 2 and comparative example 2, 10% starch slurry was used in preparation example 4 and comparative example 4, and 8% starch slurry was used in preparation example 5 and comparative example 5), granulated and dried in fluidized bed; the dried granules were placed in a three-dimensional mixer, and then added with a lubricant for total mixing; the final mixed material was tabletted in a rotary tablet press.

Preparation examples 3, 6, 11 as well as comparative examples 3, 6, 11 employed a dry granulation method: a 60-mesh sieve was selected according to the material properties, and the materials were sieved for use; the active ingredient, the excipient, the disintegrant and the disintegrant assistant (which was not added in comparative examples) were poured into a three-dimensional mixer for mixing, and granulated in a dry granulator; the obtained granules were placed in a three-dimensional mixer, and then added with a lubricant for final mixing; the final mixed material was tabletted in a rotary tablet press.

The disintegration experiments were carried out according to the following experimental conditions, and the disintegration time of each preparation example and comparative example is shown in Table 4 below.

Instrument: ZBS-6E intelligent disintegration tester (Tianjin Tianda Tianfa Technology Co., Ltd.)
Method: hanging basket method
Medium: 0.1 M HCl medium containing 0.5% Tween 80
Round trip frequency: 30-32 times per minute
Temperature: 37° C.

TABLE 4

Tablet formula and disintegration time

| formula composition | | ingredient content/(mg/tablet) in comparative examples | | | | | | | | | | |
|---|---|---|---|---|---|---|---|---|---|---|---|---|
| | | 1 | 2 | 3 | 4 | 5 | 6 | 7 | 8 | 9 | 10 | 11 |
| active integrant | crystalline form I | 21 | | | | | | 6 | 18 | 4 | 10 | |
| | crystalline form II | | 24 | 30 | 17 | 21 | 21 | 15 | 3 | 17 | 11 | 21 |
| excipient | lactose | | 125 | | | | | | | | | |
| | mannitol | 50 | | | | 110 | 156 | 108 | | 117 | 137 | 137 |
| | cellulose lactose | | | 120 | 60 | | | | | | | 20 |
| | microcrystalline cellulose | 11 | | | | 30 | | | | | | |
| | mannitol-starch | | | | | | | | | 100 | | |
| disintegrant | cross-linked sodium carboxymethyl cellulose | 8 | 15 | 25 | | | | 12 | | | | |
| | cross-linked povidone | | | | 6 | | 16 | | 10 | 10 | 10 | 10 |
| | low degree substituted hydroxypropyl cellulose | | | | | 15 | | | | | | |
| binder | povidone | | 15 | | | | | | | | | |
| | starch | | | | 10 | 10 | | | | | | |
| disintegrant assitant | sodium bicarbonate | | | | | | | | | | | |
| | sodium carbonate | | | | | | | | | | | |
| | magnesium carbonate | | | | | | | | | | | |
| | glycine | | | | | | | | | | | |
| | sodium carbonate | | | | | | | | | | | |
| | sodium sesquicarbonate | | | | | | | | | | | |
| | sodium chloride | | | | | | | | | | | |
| | glucose | | | | | | | | | | | |
| lubricant | magnesium stearate | 3 | 6 | 5 | 3 | | | 4.5 | | 2 | 2 | 2 |
| | sodium stearyl fumarate | | | | | 5 | 8 | | 6 | | | |
| tablet hardness (kg/mm²) | | 3-10 | 3-10 | 4-6 | 4-6 | 4-6 | 4-6 | 3-10 | 4-6 | 4-6 | 4-6 | 4-6 |
| tablet weight difference (within %) | | ±5 | ±5 | ±5 | ±5 | ±5 | ±5 | ±5 | ±5 | ±5 | ±5 | ±5 |
| disintegration time | | >15 min | >15 min | >15 min | >15 min | >15 min | >15 min | >15 min | >15 min | >15 min | >15 min | >15 min |
| formula composition | | ingredient content/(mg/tablet) in preparation examples | | | | | | | | | | |
| | | 1 | 2 | 3 | 4 | 5 | 6 | 7 | 8 | 9 | 10 | 11 |
| active integrant | crystalline form I | 21 | | | | | | 6 | 18 | 4 | 10 | |
| | crystalline form II | | 24 | 30 | 17 | 21 | 21 | 15 | 3 | 17 | 11 | 21 |

TABLE 4-continued

Tablet formula and disintegration time

| category | ingredient | 1 | 2 | 3 | 4 | 5 | 6 | 7 | 8 | 9 | 10 | 11 |
|---|---|---|---|---|---|---|---|---|---|---|---|---|
| excipient | lactose | | 125 | | | | | | | | | |
| | mannitol | 50 | | | | 110 | 156 | 108 | | 117 | 137 | 137 |
| | cellulose lactose | | | 120 | 60 | | | | | | | 20 |
| | microcrystalline cellulose | 11 | | | | 30 | | | | | | |
| | mannitol-starch | | | | | | | | 100 | | | |
| disintegrant | cross-linked sodium carboxymethyl cellulose | 8 | 15 | 25 | | | | 12 | | | | |
| | cross-linked povidone | | | | 6 | | 16 | | 10 | 10 | 10 | 10 |
| | low degree substituted hydroxypropyl cellulose | | | | | 15 | | | | | | |
| binder | povidone | | 15 | | | | | | | | | |
| | sarch | | | | 10 | 10 | | | | | | |
| disintegrant assitant | sodium bicarbonate | 8 | | | | | | 4.5 | 15 | | | 10 |
| | sodium carbonate | | 15 | | | 15 | | | | | | |
| | magnesium carbonate | | | | | 9 | | | | | | |
| | glycine sodium carbonate | | | 20 | | | | | | | | |
| | sodium sesquicarbonate | | | | 4 | | | | | | | |
| | sodium chloride | | | | | | | | | 50 | | 20 |
| | glucose | | | | | | | | | | 30 | |
| lubricant | magnesium stearate | 3 | 6 | 5 | 3 | | | 4.5 | | 2 | 2 | 2 |
| | sodium stearyl fumarate | | | | | 5 | 8 | | 6 | | | |
| tablet hardness (kg/mm²) | | 3-10 | 3-10 | 4-6 | 4-6 | 4-6 | 4-6 | 3-10 | 4-6 | 4-6 | 4-6 | 4-6 |
| tablet weight difference (within %) | | ±5 | ±5 | ±5 | ±5 | ±5 | ±5 | ±5 | ±5 | ±5 | ±5 | ±5 |
| disintegration time | | <60 s | <60 s | <60 s | <60 s | <60 s | <60 s | <60 s | <60 s | <120 s | <120 s | <120 s |

It turns out from the results that the oral solid preparation has an excellent disintegration speed and the preparation method thereof is simple.

Example 13: Comparative Pharmacokinetic Test

Drugs and reagents: The crystalline form I, the crystalline form II, a mixture of the crystalline form I and the crystalline form II (a weight ratio of the crystalline form I and the crystalline form II in the mixture thereof is 1:3), the crystalline form III and the amorphous form of the compound (A) were employed as test samples in this study with purity of more than 99%, and sodium carboxymethylcellulose of pharmaceutical grade was employed as an excipient.

Test animals: SD rats were randomly divided into 6 groups. Each group has 6 rats, in which half male and half female.

Drug preparation: An appropriate volume of 0.5% (w/v) sodium carboxymethylcellulose aqueous solution was added to samples according to the weight of each sample to make the final concentration of the drug 0.15 mg/ml, and each mixture was stirred under a magnetic stirrer for use.

Administration and sample collection: each sample to be tested was intragastrically administered to a fasted SD rat at a dose of 10 ml/kg. 0.3 ml of blood was collected into the anti-coagulation tube of EDTA-K2 at 15 min, 30 min, 1 h, 2 h, 4 h, 6 h, 8 h, 10 h and 24 h after administration, and centrifuged under 3000 g for 10 min at 4° C., with the supernatant taken and saved at −80° C. to be tested.

Compound (B) and azilsartan in the plasma of the samples were analyzed by LC-MS/MS (AB Sciex, API 3500 QTRAP). Compound (B) was not detected in the plasma of the animals sampled at each time point, since each test substance was rapidly converted into azilsartan in the animal body after administration. The pharmacokinetics parameters of azilsartan in the plasma of the animals after administration of the test substance are as follows:

TABLE 5

Results of comparative pharmacokinetic test

| | AUClast (ng/mL*hr) | AUCINF (ng/mL*hr) | T½ (hr) | Cmax (ng/mL) | Tmax (hr) |
|---|---|---|---|---|---|
| crystalline form I | 17987 ± 4411 | 18606 ± 4994 | 7.29 ± 1.36 | 3410 ± 1195 | 0.46 ± 0.29 |
| crystalline form II | 19004 ± 4977 | 20972 ± 6525 | 7.72 ± 1.76 | 4138 ± 695 | 0.50 ± 0.00 |
| crystalline form III | 13042 ± 2865 | 14299 ± 2636 | 7.99 ± 2.57 | 3082 ± 767 | 0.25 ± 0.00 |

TABLE 5-continued

Results of comparative pharmacokinetic test

| | AUClast (ng/mL*hr) | AUCINF (ng/mL*hr) | T½ (hr) | Cmax (ng/mL) | Tmax (hr) |
|---|---|---|---|---|---|
| mixture of crystalline form I and crystalline form II | 20709 ± 4263 | 22422 ± 5035 | 7.47 ± 0.88 | 4785 ± 675 | 0.50 ± 0.00 |
| amorphous form | 9445 ± 3623 | 10419 ± 3649 | 7.89 ± 1.96 | 1955 ± 1445 | 0.46 ± 0.29 |

Conclusion: in the above experiments, the crystalline forms or mixture of crystalline forms of the oral solid preparation have good bioavailability, which are superior to the amorphous form.

What is claimed is:

1. An oral solid preparation comprising an active ingredient, a disintegrant, a disintegrant assistant, an excipient, and a lubricant, wherein the active ingredient comprises a crystalline form of the compound of formula (A):

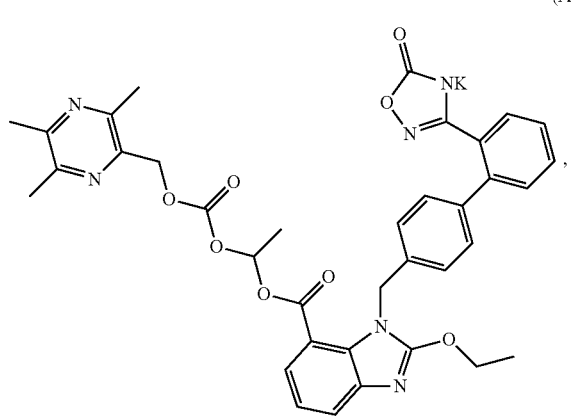

(A)

wherein the crystalline form of the compound of formula (A) is selected from at least one from the group consisting of crystalline form I, crystalline form II, crystalline form III, and crystalline form IV,
wherein, an X-ray powder diffraction pattern of the crystalline form I comprises characteristic peaks at diffraction angles (2-Theta) of 5.3±0.2°, 8.6±0.2°, 13.3.±0.2°, 20.1.±0.2°,
an X-ray powder diffraction pattern of the crystalline form II comprises characteristic peaks at diffraction angles (2-Theta) of 4.7±0.2°, 7.3±0.2°, 9.6±0.2°, 15.2±0.0.2°, and 26.3±0.2°,
an X-ray powder diffraction pattern of the crystalline form III comprises characteristic peaks at diffraction angles (2-Theta) of 5.2±0.2°, 8.0±0.2°, 12.4±0.2°, and 13.6±0.2°, and
an X-ray powder diffraction pattern of the crystalline form IV comprises characteristic peaks at diffraction angles (2-Theta) of 7.4±0.2°, 14.7±0.2°, 16.0±0.2°, 8.4±0.2°, 22.6±0.2°, 23.2±0.2°, and 29.7±0.2°.

2. The oral solid preparation according to claim 1, wherein, based on a total weight of the oral solid preparation, a content of the active ingredient is about 5-50% by weight, a content of the disintegrant is about 1-20% by weight, a content of the disintegrant assistant is about 0.1-35% by weight, a content of the excipient is about 20-80% by weight, a content of the lubricant is about 0.25-10% by weight, and a weight ratio of the disintegrant to the disintegrant assistant is from 10:1 to 1:10.

3. The oral solid preparation according to claim 2, wherein the disintegrant is a hygroscopic swelling type disintegrant selected from dry starch, croscarmellose sodium, sodium carboxymethylcellulose, calcium carboxymethylcellulose, sodium carboxymethyl starch, methylcellulose, low degree substituted hydroxylpropyl cellulose, crospovidone, chitosan, and microcrystalline cellulose.

4. The oral solid preparation according to claim 2, wherein the disintegrant assistant is a soluble small molecule selected from sodium chloride, glucose, fructose, xylitol, and mixtures thereof, or
a gas generating type salt selected from sodium carbonate, calcium carbonate, potassium carbonate, calcium magnesium carbonate, zinc carbonate, magnesium carbonate, ammonium carbonate, sodium glycinate carbonate, sodium sesquicarbonate, sodium hydrogencarbonate, calcium hydrogencarbonate, potassium hydrogencarbonate, ammonium hydrogencarbonate, and mixtures thereof.

5. The oral solid preparation according to claim 2, wherein the excipient is selected from starch, lactose, mannitol, cellulose lactose, microcrystalline cellulose, calcium hydrogen phosphate, mannitol-starch complex, and mixtures thereof; and
the lubricant is selected from talcum powder, magnesium stearate, calcium stearate, colloidal silica, hydrated silica, sodium octadecyl fumarate, polyethylene glycol, sodium stearyl fumarate, glyceryl monostearate, hydrogenated vegetable oil, and mixtures thereof.

6. The oral solid preparation according to claim 2, wherein the oral solid preparation further comprises a binder selected from starch, pregelatinized starch, dextrin, and maltodextrin, methylcellulose, carboxy methylcellulose sodium, hydroxypropylcellulose, hypromellose, ethylcellulose, microcrystalline cellulose, gelatin, gum arabic, locust gum, peach glue, polyethylene glycol, povidone, glycerol dibehenate, carbomer, polyvinyl alcohol, poly(meth)acrylic resin, sucrose, liquid glucose, maltose alcohol, corn gluten, sodium alginate, and monolaurate.

7. A method for treating hypertension, comprising administering an effective amount of the oral solid preparation according to claim 1 to a subject in need thereof.

8. The oral solid preparation according to claim 1, wherein, based on a total weight of the oral solid preparation,
a content of the active ingredient is about 8-30% by weight, a content of the disintegrant is about 2-18% by weight, a content of the disintegrant assistant is about 0.5-30% by weight, a content of the excipient is about 30-80% by weight, a content of the lubricant is about 0.5-8% by weight, and a weight ratio of the disintegrant to the disintegrant assistant is from 8:1 to 1:8.

9. The oral solid preparation according to claim 1, wherein, based on a total weight of the oral solid preparation,
a content of the active ingredient is about 10-20% by weight, a content of the disintegrant is about 4-15% by weight, a content of the disintegrant assistant is about 1-25% by weight, a content of the excipient is about 50-80% by weight, a content of the lubricant is about 1-5% by weight, and a weight ratio of the disintegrant to the disintegrant assistant is from 5:1 to 1:5.

10. A method for treating hypertension, chronic heart failure, diabetic nephropathy, wherein the method comprises administering the oral solid preparation according to claim 2 to a subject in need thereof.

11. A method for treating hypertension, chronic heart failure, diabetic nephropathy, wherein the method comprises administering the oral solid preparation according to claim 3 to a subject in need thereof.

12. A method for treating hypertension, chronic heart failure, diabetic nephropathy, wherein the method comprises administering the oral solid preparation according to claim 4 to a subject in need thereof.

13. A method for treating hypertension, chronic heart failure, diabetic nephropathy, wherein the method comprises administering the oral solid preparation according to claim 5 to a subject in need thereof.

14. A method for treating hypertension, chronic heart failure, diabetic nephropathy, wherein the method comprises administering the oral solid preparation according to claim 6 to a subject in need thereof.

* * * * *